United States Patent [19]

Tsukamoto et al.

[11] Patent Number: 5,362,640
[45] Date of Patent: Nov. 8, 1994

[54] ORNITHINE CARBAMOYL TRANSFERASE GENE AND UTILIZATION OF THE DNA

[75] Inventors: Akira Tsukamoto, Tokyo; Mieko Matsufuji, Kawaguchi; Yukio Kita, Tokyo, all of Japan

[73] Assignee: Oji Paper Co., Ltd., Tokyo, Japan

[21] Appl. No.: 27,986

[22] Filed: Mar. 8, 1993

[30] Foreign Application Priority Data

Mar. 9, 1992 [JP] Japan .................. 4-050513
Apr. 23, 1992 [JP] Japan .................. 4-104549

[51] Int. Cl.$^5$ .................. C12N 15/00; C12N 1/14; C07H 17/00; C12P 21/04
[52] U.S. Cl. .................. 435/172.3; 435/254.11; 435/320.1; 435/69.1; 435/71.1; 536/23.2; 536/23.7; 536/24.1; 536/23.74
[58] Field of Search .................. 356/23.2, 23.7, 24.1, 356/23.74; 435/172.3, 243, 320.1, 69.1, 71.1, 254.11

[56] References Cited

FOREIGN PATENT DOCUMENTS 0184438 6/1986 European Pat. Off. .
0388166 9/1990 European Pat. Off. .

OTHER PUBLICATIONS

Upshall et al. 1986. MGG 204:349–354.
Hahm et al. 1988. Appl. Environ. Microbiol. 54:1610–1611.

Primary Examiner—David T. Fox
Assistant Examiner—Elizabeth C. Kemmerer
Attorney, Agent, or Firm—Armstrong, Westerman, Hattori, McLeland & Naughton

[57] ABSTRACT

This invention relates to a novel ornithine carbamoyl transferase (OCTase) gene, a recombinant DNA containing the OCTase DNA, a transformation system for a basidiomycete, and production of useful proteins using the system.

More particularly, this invention relates to the OCTase gene of *Coriolus hirsutus* to afford an efficient host-vector system in basidiomycetes (particularly a white rot fungus such as *Coriolus hirsutus* IFO 4917) for the preparation of useful proteins. OCTase is the enzyme to transform ornithine to citrulline in arginine biosynthesis in organisms. The present invention provides the OCTase genes of *C. hirsutus*, the useful Arg⁻auxotrophic mutant of *C. hirsutus* deficient in the OCTase gene, the efficient condition for the preparation of protoplasts and the transformation of the mutant with the cloned OCTase gene and the recombinant DNA's including a promoter, a signal peptide-coding DNA and a protein-coding DNA, the construction of the novel host-vector system of *C. hirsutus*, and the new method of a large scale preparation of useful proteins using this novel host-vector system with a new recombinant DNA technique.

Furthermore, this invention provides a highly efficient method to produce a useful protein such as lignin peroxidase which is difficult to produce by the conventional method.

17 Claims, 12 Drawing Sheets

Fig.6

Fragment-1

```
                              ValAlaSerLeuAlaValAlaHisAla
 AGCT T                       GTCGCCTCTCTCGCTGTGGCCCATGCC -3'
      A                   ←←←←3'-CGCCGACACCGGGTACGGp-5' primer
HindIII site
              Phenoloxidase promoter & signal peptides region
```

+

Fragment-3

```
          AlaLeuThrLysArg ValAlaCysProAspGlyLysAsn
5'-pGCATTGACGAAACGC GT-3' →→→→→→→→
3'- CGTAACTGCTTTGCG CAGCCGGACGGGGCTGCCGTTCTTGTGGCGCTGCTTG    C AGCT
    Pro-region     ↑ Ligninperoxidase structure gene        SalI site
```

↓ pUC18 HindIII, SalI digests

↓ T4 DNA ligase
  E.coli JM109 strain transformation pPSproHL1 6.5kb

- HindIII
- Phenoloxidase promoter region
- EcoRI
- Phenoloxidase signal peptides
- Ligninperoxidase pro-peptides
- Ligninperoxidase mature type gene
- SalI

Fig.7

Fragment-4

EcoRI site

```
AATT C        CCAGTCGTCCTCTCATCCGCTCCTTGACCCGCC -3'
     G        ←←←←←←←←←GGCGAGGAACTGGGCGGp-5'
```

OCTase promoter region

+

Fragment-5

HindIII site

```
5'-pATGGCGTTCAAGGCTCT→→→→→→→→        A
3'- TACCGCAAGTTCCGAGAAGAGAGGCGGCAGAGGGA   T TCGA
```

Ligninperoxidase structure gene

↓ pUC19 HindIII, EcoRI digests

T4 DNA ligase
E.coli JM109 strain transformation

↓ pRPgHL1
5.0kb

EcoRI
NcoI — OCTase promoter region
NcoI
Ligninperoxidase structure gene
HindIII

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 375 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: Coriolus hirsutus
        ( B ) STRAIN: IFO 4917

( x i ) SEQUENCE DESCRIPTION: SEQ ID NO:1:

```
Met Ala Leu Ser Thr Lys Val Pro His Leu Met Thr Leu Ala Asp Leu
 1               5                  10                  15

Thr Pro Gly Gln Ile Gln Arg Ile Ile Thr His Ser Tyr His Leu Lys
            20                  25                  30

Arg Thr Ala Gln Pro Trp Leu Ala Pro Gln Gly Arg Ala Gly Ser Gly
        35                  40                  45

Gly Lys Tyr Ser Asn Ala Pro His Lys Leu Arg Met Pro Ser Gln Ser
    50                  55                  60
```

```
Arg  Thr  Ala  Gln  Pro  Trp  Leu  Ala  Pro  Gln  Gly  Arg  Ala  Gly  Ser  Gly
          35                      40                      45

Gly  Lys  Tyr  Ser  Asn  Ala  Pro  His  Lys  Leu  Arg  Met  Pro  Ser  Gln  Ser
     50                       55                      60

Leu  Phe  Ser  Lys  Ser  Ile  Ala  Leu  Leu  Phe  Ser  Lys  Arg  Ser  Thr  Arg
65                       70                      75                           80

Thr  Arg  Leu  Ser  Ala  Glu  Thr  Ala  Ala  Leu  Leu  Leu  Gly  Gly  Gln  Ala
                    85                       90                      95

Leu  Phe  Leu  Gly  Arg  Glu  Asp  Ile  Gln  Leu  Gly  Val  Asn  Glu  Thr  Val
               100                     105                      110

Pro  Asp  Ser  Ala  Arg  Val  Ile  Gly  Gly  Met  Cys  Gln  Gly  Ile  Phe  Ala
          115                     120                      125

Arg  Val  Gly  Asp  His  Ser  Glu  Ile  Glu  Glu  Leu  Ala  Arg  Tyr  Ser  Pro
130                               135                     140

Val  Pro  Val  Leu  Asn  Ala  Leu  Ser  Ser  Leu  Trp  His  Pro  Thr  Gln  Val
145                      150                     155                          160

Leu  Ala  Asp  Ile  Leu  Thr  Leu  His  Glu  His  Ala  Ala  Leu  Phe  Asp  Pro
               165                     170                          175

Ala  Ser  Ala  Ser  Pro  Thr  Pro  Ser  Ala  Ala  Asp  Ala  Phe  Ser  Gln  Lys
               180                     185                     190

Tyr  Thr  Lys  Leu  Gly  Glu  Val  Gly  Pro  Leu  Thr  Val  Ala  Tyr  Val  Gly
          195                     200                     205

Asp  Ser  Ala  Asn  Val  Leu  His  Asp  Met  Leu  Val  Thr  Tyr  Pro  Arg  Leu
     210                      215                     220

Gly  His  Gln  Leu  Ala  Val  Ala  Ser  Pro  Glu  Asn  Asp  Arg  Tyr  Arg  Ala
225                           230                     235                     240

Pro  Lys  Ala  Val  Trp  Asp  Arg  Val  Val  Glu  Leu  Gly  Cys  Asp  Lys  Asn
                    245                     250                          255

Ile  Phe  Trp  Thr  Ala  Asp  Pro  Arg  Ala  Ala  Val  Lys  Gly  Ala  Asp  Leu
               260                     265                     270

Val  Val  Thr  Asp  Thr  Trp  Ile  Ser  Met  Gly  Gln  Glu  Ala  Glu  Lys  Ala
          275                     280                     285

Gln  Arg  Leu  Lys  Asp  Phe  Ala  Gly  Tyr  Gln  Val  Thr  Glu  Ala  Leu  Cys
     290                      295                     300

Arg  Glu  Gly  Gly  Ala  Asn  Pro  Asp  Trp  Lys  Phe  Met  His  Cys  Leu  Pro
305                          310                     315                      320

Arg  Lys  Gln  Asp  Glu  Val  Asp  Asp  Glu  Val  Phe  Tyr  Gly  Pro  Arg  Ser
                    325                     330                          335

Leu  Val  Phe  Gln  Glu  Ser  Asp  Asn  Arg  Lys  Trp  Thr  Ile  Met  Ala  Leu
               340                     345                     350

Phe  Asp  Leu  Leu  Phe  Gly  Lys  Trp  Ser  Leu  Leu  Ala  Arg  Asn  Gly  Glu
          355                     360                     365

Gly  Ala  Asp  Ala  Gly  Ser  Glu
370                     375
```

( 2 ) INFORMATION FOR SEQ ID NO:3:

( i ) SEQUENCE CHARACTERISTICS:
        ( A ) LENGTH: 1280 base pairs
        ( B ) TYPE: nucleic acid
        ( C ) STRANDEDNESS: single
        ( D ) TOPOLOGY: linear ( i i ) MOLECULE TYPE: cDNA ( i v ) ANTI-SENSE: NO ( v i ) ORIGINAL SOURCE:
        ( A ) ORGANISM: Coriolus hirsutus (B) STRAIN: IFO 4917

(ix) FEATURE:
(A) NAME/KEY: matpeptide
(B) LOCATION: 78..1202

(xi) SEQUENCE DESCRIPTION: SEQ ID NO:3:

| | | | | | |
|---|---|---|---|---|---|
| GCACAGAGCG | ACAGCCTGAC | TCGTCCCGCG | CGCCTCCCAA | CCGGCCAGTC | GTCCTCTCAT | 60
| CCGCTCCTTG | ACCCGCCATG | GCGCTCTCGA | CGAAAGTGCC | GCACCTGATG | ACGCTCGCGG | 120
| ACCTGACCCC | GGGCCAGATC | CAGCGCATCA | TCACGCACTC | CTACCACCTC | AAGCGCACCG | 180
| CCCAGCCCTG | GCTCGCGCCC | CAGGGGCGCG | CAGGCAGCGG | CGGCAAGTAC | AGCAACGCCC | 240
| CGCACAAGCT | GCGCATGCCG | TCGCAGTCGC | TGTTCAGCAA | GTCCATCGCC | CTCCTGTTTT | 300
| CAAAGCGGAG | CACGCGCACG | CGGCTCTCCG | CCGAGACCGC | CGCCCTCCTC | CTCGGCGGGC | 360
| AGGCGCTCTT | CCTCGGGCGG | GAGGACATCC | AGCTCGGCGT | GAACGAGACC | GTGCCCGACT | 420
| CGGCGCGGGT | CATCGGCGGG | ATGTGCCAGG | GCATCTTCGC | GCGGGTGGGG | GACCATTCCG | 480
| AGATCGAGGA | ACTCGCCCGG | TACTCGCCCG | TGCCGGTGCT | CAACGCGCTC | TCCTCGCTCT | 540
| GGCACCCGAC | GCAGGTGCTC | GCGGACATCC | TCACGCTGCA | CGAGCACGCC | GCGCTCTTCG | 600
| ACCCGGCCTC | CGCGAGCCCC | ACGCCCTCCG | CCGCGGACGC | GTTCTCGCAA | AAGTACACCA | 660
| AGCTCGGCGA | GGTGCGCCCG | CTCACGGTCG | CGTACGTCGG | CGACAGCGCG | AACGTCCTGC | 720
| ACGACATGCT | CGTCACGTAC | CCGCGCCTCG | GCCACCAGCT | GCGCGTCGCG | AGCCCCGAGA | 780
| ACGACAAGTA | CCGCGCGCCG | AAGGCGGTGT | GGGACCGCGT | CGTCGAGCTC | GGCTGCGATA | 840
| AGAACATCTT | CTGGACGGCG | GACCCGCGGG | CGGCGGTGAA | GGGCGCCGAT | TTGGTCGTTA | 900
| CTGACACCTG | GATCTCGATG | GGCCAAGAGG | CCGAGAAGGC | ACAGCGACTG | AAAGACTTTG | 960
| CAGGCTACCA | AGTGACGGAG | GCGCTGTGCC | GGGAAGGCGG | GGCCAACCCG | GACTGGAAGT | 1020
| TTATGCATTG | TCTTCCTCGG | AAGCAGGACG | AGGTGGACGA | CGAGGTGTTC | TACGGGCCGC | 1080
| GATCGCTGGT | GTTCCAGGAG | TCGGACAACC | GGAAGTGGAC | GATCATGGCG | TTGTTCGACC | 1140
| TTCTCTTTGG | AAAATGGTCG | CTGCTCGCGC | GGAACGGGGA | GGGCGCAGAT | GCGGGGTCGG | 1200
| AGTAGACACA | GATAGCGTAG | ACGGAGTAAT | GCTGGCACAA | CGAACGTCTG | TCCGTGCGGG | 1260
| GTAAAAAAAA | AAAAAAAAA | | | | | 1280

(2) INFORMATION FOR SEQ ID NO:4:

(i) SEQUENCE CHARACTERISTICS:
(A) LENGTH: 2540 base pairs
(B) TYPE: nucleic acid
(C) STRANDEDNESS: single
(D) TOPOLOGY: linear (ii) MOLECULE TYPE: DNA (genomic)

(iv) ANTI-SENSE: NO (vi) ORIGINAL SOURCE:
(A) ORGANISM: Coriolus hirsutus
(B) STRAIN: IFO 4917

(ix) FEATURE:
(A) NAME/KEY: matpeptide
(B) LOCATION: 653..2340

(ix) FEATURE:
(A) NAME/KEY: intron
(B) LOCATION: 1064..1116

(ix) FEATURE:
(A) NAME/KEY: intron
(B) LOCATION: 1539..1928

(ix) FEATURE:

( A ) NAME/KEY: intron
( B ) LOCATION: 2083..2140

( i x ) FEATURE:
( A ) NAME/KEY: intron
( B ) LOCATION: 2215..2276

( x i ) SEQUENCE DESCRIPTION: SEQ ID NO:4:

```
GAATTCTGAA GCTCTCCGGC AGCCGTTCGT GTGCAAACGT GAAGGTCGTC ATCGAGCCCT      60
CCGTCTCCAA CTTCCGTGCC TCAGCGCGCG TCGTCGGCAA CTTCCCGTCA TGCTTGAACC     120
CCTCCTTCCC AAGCTCGACC GCAAGCCACC GCGGGAAATG GAAGCGAAAG ATAGCGTCGG     180
GACGCGCTAT CTCGGGGGCC GGGCGCGACG GCGGGCGATG CGAGATGTAG AGGCGCTGCC     240
AGCGCGCGAC GATCAAAATC TGGGTGACGC GTTTCGGCGC TTAATGTGAC CCGTGACATC     300
ACGCGTTTCC ATACTTTTAG CGCCCACTAG TAGTATAACA TCTGGAGATA AACCTCCAAT     360
TGTATAACAT GCCCCGACTT CAGCTGGGCA GACCCCATGG CATGTGAACA ATATATGATA     420
CAGTATATAC TGTGCTACAC AATGGCACCA TCGGCCTGCC AGGCTATATC CCTCATGTCT     480
AGGGGCCAAT CCGGCGCCAG TTCCATACCG TTGGCGCCCG CGAGCATCCG GGTGACAAGG     540
TGTGTAGGCG CCCGAGACTC CTCTACCAGC GACGGCACAG AGCGACAGCC TGACTCGTCC     600
CGCACGACTC TCAACCGCGC CAGTCGTCCT CTCATCCGCT CCTTGACCCG CCATGGCGCT     660
CTCGACGAAA GTGCCGCACC TGATGACGCT CGCGGACCTG ACCCCGGGCC AGATCCAGCG     720
CATCATCACG CACTCCTACC ACCTCAAGCG CACCGCCCAG CCCTGGCTCG CGCCCCAGGG     780
GCGCGCAGGC AGCGGCGGCA AGTACAGCAA CGCCCCGCAC AAGCTGCGCA TGCCGTCGCA     840
GTCGCTCTTC AGCAAGTCCA TCGCCCTCCT GTTTTCGAAG CGGAGCACGC GCACGCGGCT     900
CTCCGCCGAG ACCGCCGCCC TCCTCCTCGG CGGGCAGGCG CTCTTCCTCG GCGGGAGGA     960
CATCCAGCTC GGCGTGAACG AGACCGTGCC GGACTCGGCG CGCGTCATCG GCGGGATGTG    1020
CCAGGGCATC TTCGCGCGCG TGGGGGACCA TTCGGAGATC GAGGTGCGTC TTTACAGCCG    1080
TGCCGTCCAC GCTCGTCACG CTCACCCATC CCCCAGGAAC TCGCCCGGTA CTCGCCCGTG    1140
CCCGTGCTCA ACGCGCTCTC CTCGCTCTGG CACCCGACGC AGGTGCTCGC GGACATCCTC    1200
ACGCTGCACG AGCACGCCGC GCTCTTCGAC CCGGCCTCCG CGAGCCCCAC GCCCTCCGCC    1260
GCCGACGCGT TCTCGCAAAA GTACACCAAG CTCGGCGAGG TGCGCCCGCT CACGGTCGCG    1320
TACGTCGGCG ACAGCGCGAA CGTGCTGCAC GACATGCTCG TCACGTACCC GCGCCTCGGC    1380
CACCAGCTGC GCGTCGCGAG CCCCGAGAAC GATAGGTACC GCGCGCCCAA GGCGGTGTGG    1440
GACCGCGTCG TCGAGCTCGG CTGCGATAAG AACATCTTCT GGACGGCGGA CCCGCGGGCG    1500
GCGGTGAAGG GCGCGGACTT GGTCGTCACT GACACCTGGT GAGTCCCCCT ATACCCTGAG    1560
TGGTGGTGAA GTGCAGGATC GCTGCGAACG TATCCGGCGC GCAAGACCTT TCTCATACGC    1620
TGCAGCTGCG TTCACGAATG CACAAACGAT GGTCAACCAC GGGCATACAA CGCTGGTGTC    1680
CGCGTAGACG CCGTCGATGG AGAGGCTCCG TCTGATATCG CGTACGGAGT GTTTACTAGC    1740
CGTAATCTTC CGGTCGCCCA ACTGTCGGAG AGCGATCTCT GCTTATGGTC GCGCACAACC    1800
TTCAAGTTCG GTCCGACAAC AGAGCTTCGG GTTGCGATTA GATTTGCCCG ACAGCATGGG    1860
CCTCTTCCGC ATCTGTTACC CTGGCGATCC ACGAACGTGT ACACAGAATA CTGACAGCTG    1920
AGTTACAGGA TCTCGATGGG CCAAGAGGCC GAGAAGGCGC AGCGACTGAA AGACTTTGCA    1980
GGGTACCAAG TGACGGAGGC GCTGTGCCGG GAAGGCGGGG CGAACCCGGA TTGGAAGTTC    2040
ATGCATTGTC TTCCTCGGAA GCAGGACGAG GTGGACGACG AGGTTCGTCG TGCGTCGATC    2100
CCGAGAATTG AGATAGGCTG ACGGGCCGC ATCGCGACAG GTGTTCTACG GGCCGCGGTC    2160
GCTGGTGTTC CAGGAGTCGG ACAACCGGAA GTGGACGATC ATGGCGTTGT TCGAGTGCGT    2220
```

| | | | | | |
|---|---|---|---|---|---|
| TCTCGCGTTA | GTTGTGCTGA | TACGCCCGAT | GTAGGAGTGC | TGATCACGTT | CTGCAGCCTT | 2280
| CTCTTTGGAA | AGTGGTCGCT | GCTCGCGCGG | AACGGGGAGG | GCGCAGATGC | GGGGTCGGAG | 2340
| TAGACACAGA | TAGCGTAGAC | GGAGTAATGC | TGGCACAACG | ATCGTCTGTC | CGTGCGGGGT | 2400
| ATGTTGCGCG | TGAATGTTCC | TGGAGACTTG | CCTGGAATGG | ACAAGATTGG | CCACGTGCCG | 2460
| CGCATGACGT | CTGCCAGTCC | GGGGTAGCGC | CCAGCCCGGC | CGAGCTCTGT | TCTCCTCCTC | 2520
| CTCCCCTTCT | TCCCTCTCTT | | | | | 2540

ORNITHINE CARBAMOYL TRANSFERASE GENE AND UTILIZATION OF THE DNA

FIELD OF THE INVENTION

This invention relates to a novel ornithine carbamoyl transferase (OCTase) gene, a recombinant DNA containing the OCTase DNA, a transformation system for a basidiomycete, and production of useful proteins using the system.

More particularly, this invention relates to the OCTase genes of *Coriolis hirsutus* to afford an efficient host-vector system in basidiomycetes (particularly a while rot fungus such as *C. hirsutus* IFO 4917) for the preparation of useful proteins.

DESCRIPTION OF THE RELATED ART

The OCTase is an enzyme to transform ornithine to citrulline in arginine biosynthesis in organisms. An Arg⁻-auxotrophic mutant deficient in the aforementioned OCTase gene can be prepared by UV irradiation or N-methyl-N'-nitro-N-nitrosoguanidine (NTG) treatment of *C. hirsutus*.

The development of the aforementioned OCTase genes of *C. hirsutus* as the marker, the Arg auxotrophic mutant of *C. hirsutus* as the host, the efficient condition for the preparation of protoplasts and the transformation of the mutant with the cloned OCTase DNA, and the recombinant DNA's including a promoter, a signal peptide-coding DNA and a protein-coding DNA, has realized the construction of the novel host-vector system of *C. hirsutus*. Thus, this novel host-vector system with a new recombinant DNA technique can provide a new method of a steady, large scale preparation of useful proteins. Furthermore, this invention provides a highly efficient method to produce a useful protein such as lignin peroxidase which is difficult to produce by the conventional method.

To date numerous efforts have been made to fulfill the purpose of realizing quantity production of a useful protein by the use of the technique of gene recombination.

The technique of gene recombination for the quantity production of a useful protein basically comprises a host, a vector and a gene coding a useful protein.

One of the established host which is useful for this purpose is a procaryote such as Escherichia Coil. However, the process of the large scale production of useful proteins is not often very promising. For example, when Escherichia coli is the host, it is very difficult to produce a useful human protein without any contamination of harmful byproducts. Therefore, it prevents simplification and economization of the large scale production of the protein.

One of the solution for the aforementioned problem is to use a lower eucaryote such as yeast as the host. However, in this case, the productivity is not acceptable for practical use so far. Thus, efforts are being continued in research and development of a host-vector system capable of more efficient production of useful proteins.

Basidiomycetes belonging to eucaryotes are much phylogenetically closer to animals than yeasts (T.L. Smith, Proc. Natl. Acad. Sci. USA, 86 7063 (1989)). Incidentally, a technique of gene recombination using a basidioncete as a host remains yet to be established. Recently, a few host-vector systems of basidiomycetes have been reported (A. Munoz-Rivas, et al., Mol. Gen. Genet., 205, 103, (1986)). However, these systems have not been accomplished for practical use so far. The basidiomycetes include numerous useful fungi such as lignin-degrading fungi remains yet to be established. Especially, genetics of *C. hirsutus* belonging to basidiomycetes has not been studied very well. Furthermore, a host-vector system of this fungus has been hitherto unknown.

SUMMARY OF THE INVENTION

The present inventors have pursued a diligent study with the focus of fulfilling the demand for development of an efficient host-vector system for the large scale preparation of useful proteins. Particularly, the demand for development of a novel suitable marker gene, a useful host, an efficient transformation method and condition, and a useful recombinant DNA of a useful protein gene including a promoter and a signal peptide-coding DNA in basidiomycetes.

They have consequently succeeded in developing novel DNA's, i.e. ornithine carbamoyl transferase (OCTase) genes of *Coriolus hirsutus* and an efficient host-vector system of the genus Coriolus for the expression, secretion and production of useful proteins in a basidiomycete in quantity large.

Accordingly, the present invention provides (1) an isolated structural gene coding for ornithine carbamoyl transferase (OCTase) of *Coriolus hirsutus*. The gene preferably coding for the amino acid sequence shown in SEQ ID NO: 1 or SEQ ID NO: 2.

The present invention also provides (2) an isolated OCTase gene comprising a structural gene coding for OCTase and a control region controlling the expression of the structural gene. The OCTase gene, preferably, essentially consists of the nucleotide sequence shown in SEQ ID NO: 4.

The present invention further provides (3) a recombinant linear or circular DNA comprising a structural gene coding for OCTase of *C. hirsutus*, or an OCTase gene comprising a structural gene coding for OCTase of *C. hirsutus* and a control sequence controlling the expression of the OCTase. The recombinant DNA provides a selectable marker showing successful transformation when a host basidiomycete is cotransformed with a DNA comprising a gene coding for a desired protein.

The present invention further provides (4) a recombinant linear or circular DNA comprising:

(a) a structural gene coding for OCTase of *C. hirsutus*, or an OCTase gene comprising a structural gene coding for OCTase of *C. hirsutus* and a control sequence for controlling the expression of the structural gene;

(b) an expression control sequence operable in a basidiomycete of the genus Coriolus; and (c) a gene coding for a desired protein under the control by the expression control sequence (b). The circular DNA is, for example, an expression plasmid for expressing the desired protein.

The present invention also provides (5) an auxotropnic mutant of a basidiomycete of the genus Coriolus deficient in an ability to express OCTase. The auxotrophic mutant is a partner of a host-vector system of the present invention.

Namely, the present invention further provides (6) a host-vector system for basidiomycete comprising the recombinant liner or circular gene (3) or (4), and an auxotrophic mutant ( 5 ) .

The present invention also provides (7) a process for production of a transformant basidiomycete of the genus Coriolus capable of expression of a desired protein comprising the steps of (a) cotransforming the abovementioned auxotrophic mutant (5) with the said recombinant linear or circular DNA (3) and a recombinant linear or circular DNA comprising a gene coding for a desired protein and a control sequence for controlling the expression of the gene coding for the desired protein, and (b) selecting a transformant capable of growing a medium lacking arginine.

The present invention further provides (8) a process for production of a transformant basidiomycete of the genus Coriolus, comprising the steps of (a) transforming the auxotrophic mutant (5) with the recombinant linear or circular DNA (4).

The present invention further provides a transformant basidiomycete obtainable by the process (8) capable producing a desired protein.

The present invention also provides (9) a process for production of a desired protein, comprising the steps of culturing a transformant basidiomycete (8) to produce the desired protein, and recovering the desired protein from the culture.

BRIEF DESCRIPTION OF THE FIGURES

FIG. 6 is the construction of a lignin peroxidase expression vector pPSproHL1 described in example 11.

FIG. 7 is the construction of a lignin peroxidase expression vector pRPgHL1 described in example 12.

DESCRIPTION OF THE PREFERRED EMBODIMENTS

Figure 1:
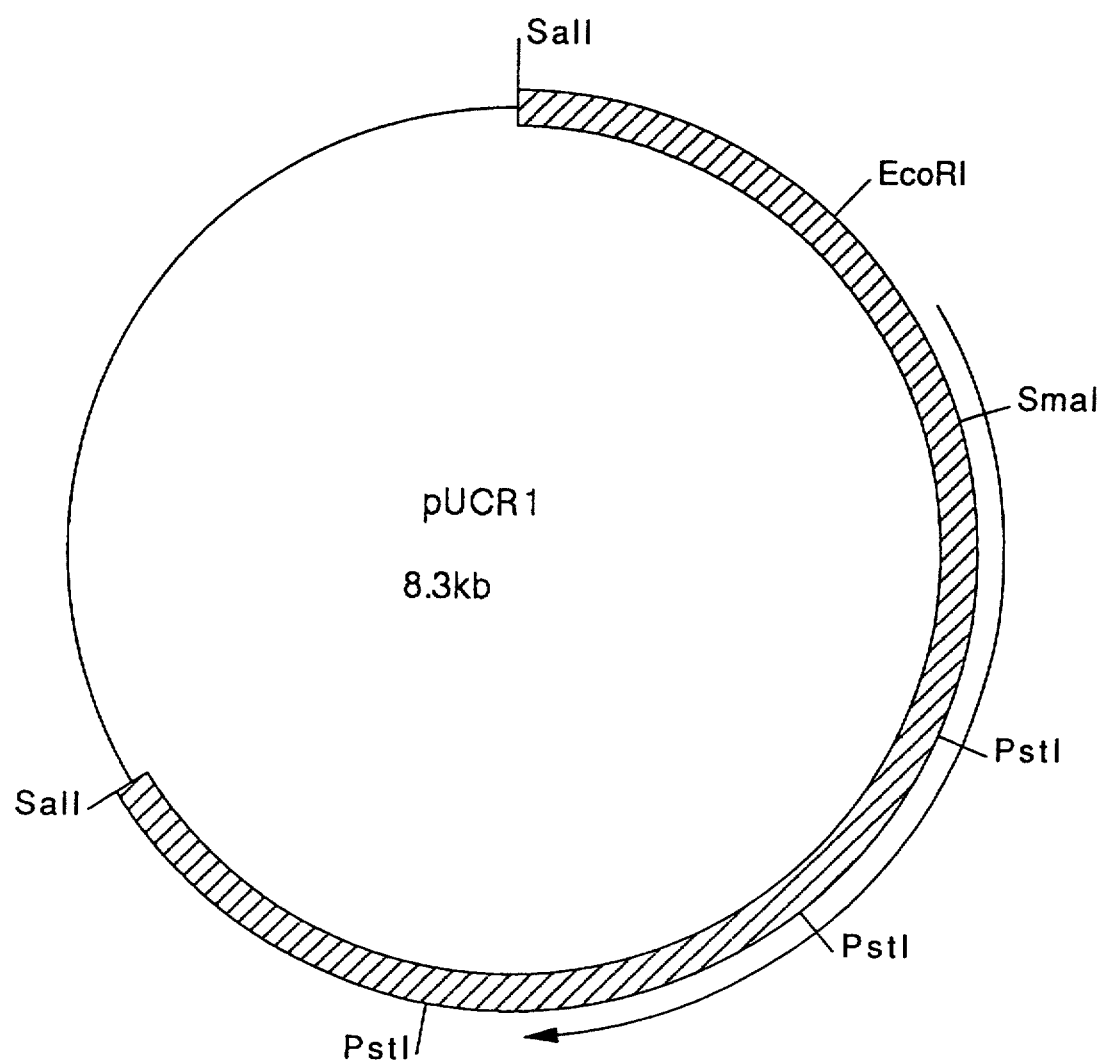
FIG. 1 is a restriction endonuclease physical map of plasmid, pUCR1.

The present inventors have studied OCTase gene of *Coriolus hirsutus* to find an efficient host-vector system in basidiomycetes for the preparation of useful proteins. They have succeeded in cloning the novel OCTase genes from the restriction endonuclease fragments of chromosome DNA of *C. hirsutus.* They have also prepared a useful Arg⁻auxotrophic mutant deficient in OCTase gene from *C. hirsutus* and established the efficient condition for the preparation of protoplasts and transformation of the mutant with the cloned OCTase DNA and recombinant DNA's including a promoter, a signal peptide-coding DNA and a protein-coding DNA. Thus they have succeeded in the construction of the novel host-vector system of *C. hirsutus.* Furthermore, they have found that this novel host-vector system using recombinant DNA technique can provide a new method of a robust, large scale production of useful proteins.

The present invention provides a DNA (I), concerning an ornithine carbamoyl transferase (OCTase) gene coding the amino acid sequence depicted in SEQ. ID NO: 1.

The present invention also provides a DNA (II), concerning an ornithine carbamoyl transferase (OCTase) gene coding the amino acid sequence depicted in SEQ ID NO: 2.

The present invention also provides a DNA (III), concerning an OCTase gene coding the DNA sequence depicted in SEQ ID NO: 3.

The present invention also provides a genomic DNA (IV), concerning an OCTase gene coding the DNA sequence depicted in SEQ ID NO: 4.

The present invention also provides a method for preparing a novel organism (particularly a white rot fungus *Coriolus hirsutus*) possessing the ability to produce a useful protein by the transformation with any of DNA (I) to (IV) and/or a recombinant DNA consisting of a functional promoter In basidiomycetes and/or a signal-peptide-coding DNA and a protein-coding DNA.

The present invention also provides a recombinant DNA as described above, consisting of a functional promoter in Coriolus species and/or a signal-peptide-coding DNA and a protein-coding DNA.

The present invention also provides the aforementioned recombinant DNA, wherein said promoter is a promoter of phenoloxidase gene, a promoter of lignin peroxidase gene or OCTase gene, and/or said signal-peptide-DNA is coding a signal peptide of phenoloxidase or a signal peptide of lignin peroxidase.

The present invention also provides a method for preparing a novel organism as described above, wherein the host cell is deficient in OCTase and the tarnsformant is screened in a medium containing no arginine.

The present invention also provides the aforementioned novel organism, wherein said organism is Coriolus species.

The present invention also provides a method for producing a protein as described above, wherein said protein is produced by culturing said cell and obtaining proteins from the resultant culture broth.

The aforementioned basidiomycete used in the cloning genomic DNA and mRNA was a strain of *C. hirsutus* (IFO 4917) obtained from the culture collection of the Institute for Fermentation, Osaka, Japan. A method for extracting total RNA constructing a cDNA library is as described below.

Total RNA was extracted from the mycelia of *C. hirsutus* cultured in a medium containing no arginine to induce the expression of OCTase gene. Poly(A) RNA was purified from the total RNA according to the method, described in Proc. Natto Acad. Sci. USA, 69, 1408 (1972), using oligo(dT) cellulose column. cDNA was synthesized in vitro from the poly(A) RNA according to the method described in Gene, 25 263 (1983), incorporated in a phage DNA λ gt according to the method described in Science, 222, 263 (1983), and packaged in vitro to afford the cDNA library for the OCTase gene cloning.

To conduct plaque hybridization for the cloning of the OCTase gene from the aforementioned cDNA library, the synthetic DNA probes synthesized based on the DNA sequences of the OCTase genes isolated from other species (B. Berse, et al., Gene, 25, 109 (1983); F. P. Buxton, et al., Gene zQ, 255 (1987) can be used. In addition, the aforementioned hybridization can be also conducted by using a fragment of the Arg B gene coding the OCTase gene of *Aspergillus nidulans* (Upshall,A., M.G.G., 204, 349 (1986)). The isolated can be sequenced by the method described by Sanger (Proc. NatL. Acad. Sci. USA, 74, 5463, (1977)). The transformed JM109/pUCRM harboring the recombinant cDNA of OCTase gene was deposited with National Institute of Bioscience and. Human-Technology, Agency of Industrial Science and Technology under FERM BP-4202.

Chromosome DNA can be purified from *C. hirsutus* using the conventional method such as described by Yelton (Proc. Natl. Acad. Sci. USA, 81, 1470 (1984)). The genomic DNA obtained was then partially digested with an appropriate restriction endonuclease, followed by a fractionation using a sucrose density gradient centrifugal separation to afford a 10 to 25 kbp genomic DNA fragment. The resultant DNA fragment was inserted to the phage DNA treated with an appropriate restriction endonuclease. For example, DNA EMBL3 (A-M, Frishauf, et al., J. Mol. Biol. 17Q, 827 (1983)) can be usea as the aforementioned phage. The recombinant phage DNA was packaged in vitro to construct a genomic DNA library. For the subcloning of the DNA can be used a conventional cloning vector, such as pUC18 (C. Yanisch-Perron, et al., Gene, 33, 103 (1985)).

Figure 5:
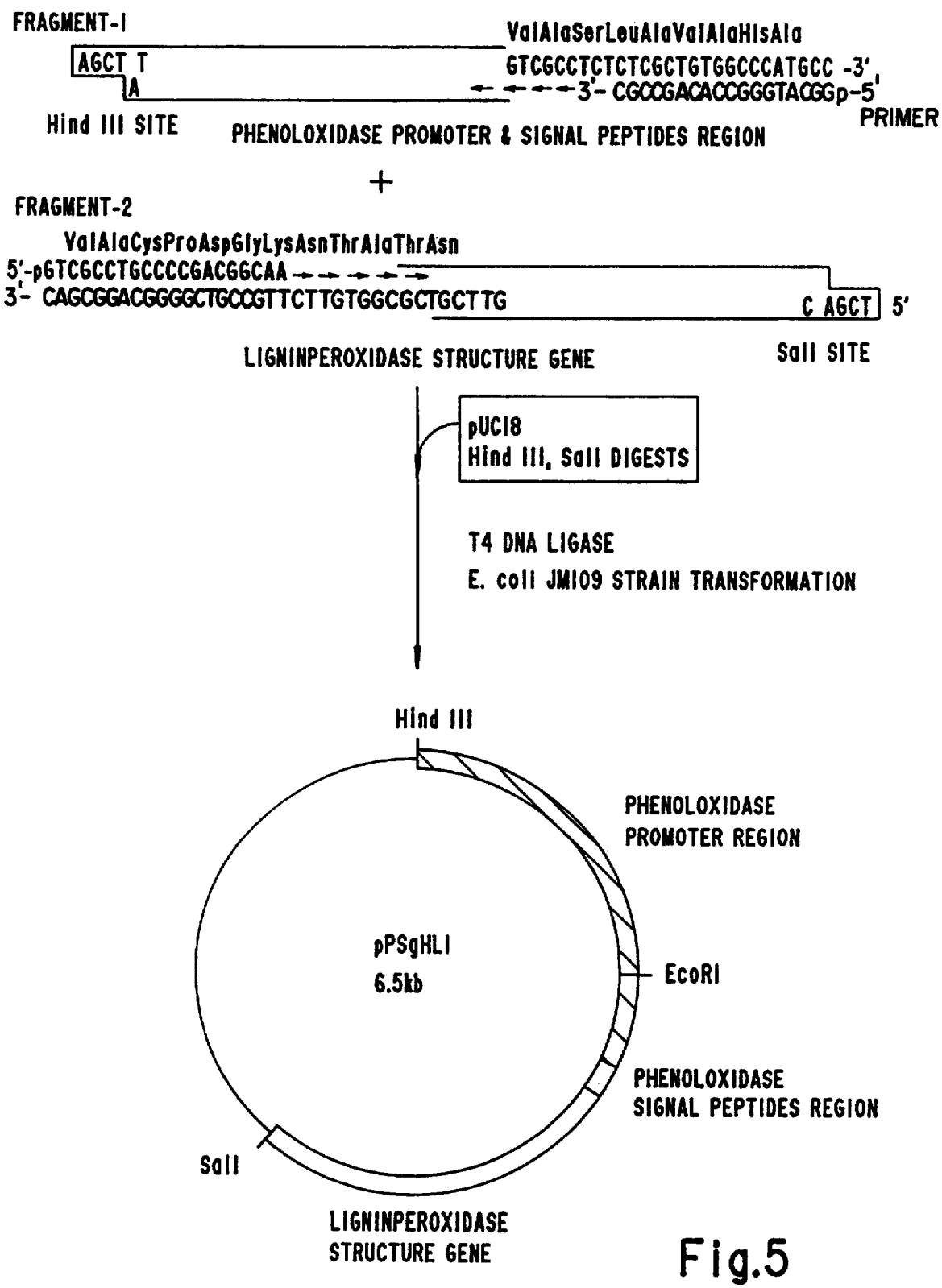
FIG. 5 is the construction of a lignin peroxidase expression vector pPSgHL1 described in example 10.

The aforementioned OCTase gene cloned from the cDNA library can be used for the probe to isolate the genomic OCTase gene from the genomic libraryas described above. The restriction endonuclease physical map is depicted in FIG. 5. The genomic OCTase gene can be inserted into an appropriate *E. coli* cloning vector, such as pUC type cloning vector, pUC18 to transform anArg⁻auxotrophic mutant of Coriolus species such as *C. hirsutus* mutant. Auxotrophic mutants of Coriolus species such as *C. hirsutus* can be prepared using the conventional method as described below.

Monokaryons of *C. hirsutus* can be prepared from colonies of mycelial protoplast regenerants as well as germinated basidiospores. Oidia formed from the monokaryons can be then subjected to irradiate with UV or treated with chemical mutagens, such as N-Methyl-N'-nitro-N-nitrosoguanidine (NTG) or ethyl methanesulfonate. The mutant can be characterized in details as described in example 5 to select the amino acid requiring mutants. In example 6, the deficiency in the amino acid biosynthetic pathway can be further determined.

Thus, the novel host-vector system of an eucaryote, *C. hirsutus* can be provided by the recombinant vector DNA containing the cloned OCTase gene of *C. hirsutus* as well as the Arg⁻auxotrophic mutant of *C. hirsutus*. The transformed Arg⁻auxotrophic mutant of *C. hirsutus*, introduced the aforementioned OCTase gene, can produce the enzyme which was deficient in the mutant. Therefore, the aforementioned OCTase gene of *C. hirsutus* contains the complete open reading frame (the protein-coding region) of the OCTase gene as well as the regulation region necessary for the expression of the OCTase gene. This conclusion can be confirmed by the existence of the promoter sequence in the upstream region of the DNA sequence of the genomic OCTase gene.

The Arg⁻auxotrophic mutant of *C. hirsutus*, OJI-1078 and the *E. coli* JM109/DUCR1 transformed with the aforementioned genomic OCTase gene were deposited with National Institute of Bioscience and Human-Technology, Agency of Industrial Science and Technology under FERM P-12677 and FERM BP-4201, respectively.

The present invention further provides a recombinant DNA for the novel host-vector system as well as a new method of a large scale production of useful proteins.

This recombinant DNA consists of a protein-coding DNA as well as a functional promoter in basidiomycetes and/or a signal-peptide-coding DNA at the 5' terminus of the protein-coding DNA.

This promoter used for the expression of the protein can be a promoter functional promoter in Coriolus species such as *C. hirsutus*. An efficient expression of the protein can be expected using the promoter of *C. hirsutus*, such as the promoter of phenoloxidase (Y. Kojima, et al., J. Biol. Chem., 265, 25, 15224 (1990)). Furthermore, the promoter of lignin peroxidase can be used for the same purpose, which was described in the Japanese Patent Application 92-60503 and also deposited as a transformed *E. coli* XL-1 blue/pBSLPOG7 harboring a plasmid pBSLPOG7 containing the aforementioned promoter with National Institute of Bioscience and Human-Technology, Agency of Industrial Science and Technology under FERM P-12683. In addition, a promoter of another lignin peroxidase gene can be also used for the same purpose, which was described in the Japanese Patent Application 92-52673 and also deposited as a transformed *E. coli* JM109/pUCL-POG4 harboring a plasmid pUCLPOG4 containing the aforementioned promoter with National Institute of Bioscience and Human-Technology, Agency of Industrial Science and Technology under FERM P-12678.

For the aforementioned signal-peptide-coding DNA can De used by any functional signal-peptide-coding DNA of Coriol species such as *C. hirsutus*, i.e. the original promoter of a useful protein a signal-peptide-coding DNA of yeast or filamentous fungi. Moreover, a synthetic DNA designed for the signal-peptide-coding DNA can be also used. These signal sequences as described above, can be a functional signal-peptide-coding DNA of *C. hirsutus* for secretionary expression, such as a signal peptide of phenoloxidase or a signal peptide of lignin peroxidase.

A useful protein which can be expressed and produced in basidiomycete, *C. hirsutus* are enzymes, growth factors, hormones, cytokinins, and virus proteins such as, for example human lisozymes, protein disulfide isomerases (PDI), human epidermal growth factors (EGF), human nerve growth factors (NGF), growth hormones, insulins, interferon $\alpha$, interferon $\beta$, interferon $\gamma$, interleukin 2, tumor necrosis factors (TNF), surface proteins of B type hepatitis, lymphotoxins, lignin peroxidases, and phenoloxidases.

The DNA sequences coding the aforementioned useful proteins can be complementary DNA's (cDNA), genomic DNA's or synthetic DNA's.

In the case of the existence of a propeptide between the signal peptide and the protein-coding sequence, the whole DNA sequence including the propeptide sequence can be used for the expression of the protein. On the contrary, in the case of a protein containing no propeptide, a propeptide DNA sequence can be inserted between the signal sequence and the protein-coding sequence.

In the case of the production of lignin peroxidase with a wild strain of *C. hirsutus*, a restricted condition such as low nitrogen content of the medium, high concentration of oxygen, statical culture is required preventing efficient large scale production of the enzyme. Cloning of the gene of lignin peroxidases. have been reported only for *Phanerochaete chrysosporium* (Nature, 326, 520, (1987)), *Coriolus versicolor* (B.B.R.C., 179, 428 (1991)), and *Phlebia radiata* (Gene, LS, 343 (1989). However, no active enzyme has been produced using the conventional method.

By using the present host-vector system of *C. hirsutus*, active lignin peroxidase can be produced efficiently using any lignin peroxidase gene, such as a genomic DNA, CDNA and a synthetic DNA.

DNA introduced for the transformation of *C. hirsutus* can be any functional marker gene in Coriolus species such as *C. hirsutus*, for example the recombinant vector DNA containing the OCTase gene. The suitable vectors which can be used in the system can be any vector DNA capable of amplifying the recombinant DNA in a host such as *E. coli* for a convenient gene manipulation, for example pUC vector, pBR322 vector or pBluescript vector. The aforementioned plasmid vector can be used as a selection marker gene as a circular form DNA and a linear form DNA as well as the OCTase gene fragment.

An expression vector of a protein such as lignin peroxidase can be constructed by the insertion of a promotel DNA ligated to the structural gene of the protein at the downstream region into the aforementioned recombinant DNA. Furthermore, more efficient expression can be obtained by the insertion of a functional terminator sequence of Coriolus species such as *C. hirsutus* at the downstream region of the protein-coding sequence such as lignin peroxidase gene.

Moreover, the aforementioned OCTase DNA and the expression vector of a protein can be co-transformed without ligating each other as a circular, linear or fragment form give the transformants.

The method to construct the aforementioned expression vector can be the conventional method described by SambrooK eE al.(Molecular Cloning A Laboratory Manual / 2nd Ed.).

Examples of the expression plasmid of the lignin peroxidase are such as pPgHLC1, pPcHLC1, pPSgHL1, pPSprOHL1, pRPgHL1, and pRPgHLC1 as described in examples 8, 9, 10, 12, and 13, respectively.

Coriolus species such as *C. hirsutus* can be transformed using those expression vectors. The transformation of protoplasts of *C. hirsutus* prepared by the method described in example 7 can be conducted by the polyethylene glycol method and the electroporation method. The preferred concentration of the polyethylene glycol for the polyethylene glycol method is in a range of 10% to 50%. The preferred concentration of calcium ion is in a range of 25 mM to 200 mM.

The resultant transformants can be cultured by the conventional method. For example, the transformant can be cultured in glucose-peptone medium at 15° to 40° C. (preferentially at 24° to 37° C.) for 7 days with or withouE shaking. Air bubbling or agitation can be used if necessary.

After completion of the culture, the culture broth can De separated from the cell bodies by the conventional method. when the product is contained in the cell, the cell bodies call be homogenized by the supersonic method, the frenchpress method, the mechanical grinding method, and the enzymatic lysis method. Optionally, the chemical method using surfactants such as triton-X100, deoxycholate can be combined to the aforementioned method. The resultant culture broth and the extracts of the cell bodies can be purified using the conventional protein purification methods, such as salt precipitation, isoelectric precipitation, gel filtration, and ion-exchange chromatography (HPLC, FPLC etc.), to obtain the product.

The activity of the lignin peroxidase obtained from the aforementioned method can be measured by the increasing absorbance of veratraldehyde produced by the oxidation of veratryl alcohol (M. Tien, et al., Proc. Natl. Acad. Sci. USA, 81, 2280 ( 1984 ) )

EXAMPLES

Now, cloning of a novel OCTase gene of *C. hirsutus*, preparation of a useful host *C. hirsutus*, development of an efficient transformation method and condition, and construction of a useful recombinant DNA of a useful protein gene including a promoter and a signal peptide-coding DNA will be described in detail below with reference to working examples. It should be noted, however, that this invention is not limited to these working examples.

EXAMPLE 1

Construction of cDNA library

A wild-type dikaryotic strain of *C. hirsutus* Quele (IFO 4917) was obtained from the culture collection of the Institute for Fermentation, Osaka, Japan. *C. hirsutus* is a species in which the basidiospore is monocleated, and the parental nuclei do not fuse after mating of two compatibie monokaryons but stay in pairs(Bose 1934). Monokaryons of *C. hirsutus* were isolated from colonies of mycelial protoplast regenerants as well as germinated basidiospores obtained from a fruit body of the dikaryotic cultures. Vegetative cultures were maintained on slants of potato-dextrose medium.

The culture media used in this invention are such as MM medium, SMY medium, GP medium, synthetic medium as described below.

The MM (minimal medium), pH 5.6, containing per liLer 10 g glucose, 1.5 g ($NH_4$)$_2$$HPO_4$, lg $K_2HPO_4$, 0.5 g $KH_2PO_4$, 1.5 g $MgSO_4$-$7H_2O$, 0.12 mg thiamine-HCl.

The SMY medium, pH 5.6, containing per liter10 g sucrose, 20 g malt extract, 4 g yeast extract.

The GP medium, pH 4.5, containing per litter 20 g of glucose, 5 g of polypeptone, 2 g of yeast extract, i g of $K_2HPO_4$, and 0.5 g of $MgSO_4$·$7H_2O$ The synthetic medium, pH5.6, containing no arginine, 2% of glucose, 0.67% of Yeast Nitrogen Base (Difco), 0.1% of $K_2HPO_4$, 0.15% of ($NH_4$)$_2$$HPO_4$, 0.05% of $KH_2PO_4$, 0.15% of $MgSO_4$·$7H_2O$, 0.12 ppm of thiamine·HCl, 40 ppm of glycine, 40 ppm of alanine, 60 ppm of valine, 70 ppm of leucine, 70 ppm isoleucine, 50 ppm of serine, 60 ppm of threonine, 60 ppm of proline, 80 ppm of phenylalanine, 90 ppm of tyrosine, 100 ppm of tryptophan, 70 ppm of lysine-HCl, 80 ppm of histidine-HCl, 120 ppm of cysteine-HCl, 70 ppm of methionine, 70 ppm of aspartic acid, and 90 ppm of glutamic acid.

In 200 ml of a GP medium *Coriolus hirsutus* IFO 4917 was shaken-cultured at 28° C. for 7 days. Then the cells were collected and washed with sterilized water. The cells were further shaken-cultured at 28° C. for 4 days in 500 mt of a synthetic medium. The cells were collected and frozen in liquefied nitrogen.

Five gram of the frozen cell bodies was ground with a mortar. The apparatuses and reagents used in the following experiment were treated with diethylpyrocarbonate according to the conventional method (Sambrook, Molecular Cloning A Laboratory Manual 2nd Ed., 1989). The extraction of the ground cell bodies was carried out by the use of a commercially available RNA extraction kit (produced by Amersham Japan K.K.) to afford total RNA. Two milligram of the total RNA was purified using a commercially available mRNA purification kit (produced by Pharmacia) to give poly (A) +RNA fraction. From 5 µg of the poly (A) +RNA, double-stranded cDNA was synthesized using a commercially available cDNA synthesizing kit (produced by Amersham Japan K.K. according to the manual. cDNA library was constructed using a commercially available λgt10 cDNA cloning kit (produced by Amersham Japan K.K.) according to the manual to obtain $5 \times 10^5$ reconbinant λ phage bodies/µg insert DNA. The cDNA library was caused to infect an E. coli NM514 strain to form 2,000–3,000 plaques / 90 mmφ plate for a cloning experiment.

EXAMPLE 2

Cloning of OCTase gene from cDNA library

The cloning of the OCTase gene was conducted according to the conventional plaque hybridization method (Sambrook, Molecular Cloning A Laboratory Manual 2nd Ed., 1989).

The following two synthetic DNA probes labeled with a radioisotope (32p) were used in the hybridization experiment.

| (A) | 5'-TTT(C)ATGCAT(C)TGT(C)CTICC-3' | 17 mer, 8 mix |
| (B) | 5'-CCA(G)TAA(G)AAA(G,C,T)ACC(T)TCA(G)TC-3' | 17 mer, 64 mix |

In addition, 0.8 kbp fragment of Sal I digest of Arg B gene of *Aspergillus nidulans* labeled with $^{32}p$ was used for the same experiment.

The plaques were transferred to a commercially available nylon membrane to iramobilize the DNA on the membrane by the conventional method. The membrane was washed with a pre-hybridization solution (5×SSC, 5×Denhardt's soiution, 1% SDS, and 100 µg/ml denatured DNA calf thymus DNA) at 65° C. overnight. The membrane was then hybridized with the hybridization solution containing $^{32}p$ labeled DNA probe at 45° C. for 24hr. The membrane was then washed, dried by the conventional method. The positive plaque was selected from the membrane by autoradiography to give a single positive clone hybridized with the aforementioned three DNA probes from 80,000 plaques.

The phage DNA was prepared from the positive clone by the conventional method, followed by the digestion with restriction endonuclease BamHI and the fractionation using agarose gel electrophoresis to obtain 1.3 kbp of BamHI DNA fragment. The DNA fragment was then subcloned into the Bam HI site of a plasmid vector pUC18 (produced by Takara Shuzo Co., Ltd. Japan) and transformed to E. Coli JM109 by the conventional method. The DNA sequence of the subcloned DNA was then determined using a sequenase kit produced by United States Biochemical Co., Ltd.

The DNA sequence was depicted in SEQ ID NO: 3 to demonstrate 1125 bp of open reading frame. The deduced amino acid sequence from the DNA sequence was then compared with the amino acid sequences of other OCTase such as Arg B of *A. nidulans* to indicate similarity among them and the consensus sequence for the carbamoyl binding region of OCTase. Therefore, the 1.3 kbp DNA fragment was identified as the OCTase gene of *C. hirsutus*. This DNA fragment was used as the probe for the cloning of the genomic OCTase gene of *C. hirsutus* as described in examples 3 and 4.

The aforementioned *E. coli* JM109/pUCRM transformed with the aforementioned OCTase CDNA gene was deposited with National Institute of Bioscience and Human-Technology, Agency of Industrial Science and Technology as FERN P-13424 on Feb. 12, 1993, and transferred to an international deposition under the Budapest Treaty, as FERM BP-4202 on Feb. 22, 1993.

EXAMPLE 3

Construction of genomic DNA library

*C. hirsutus* IF04917 was shaken-cultured at 28° C. for 7 days in GP medium as described in example 1. The cells were collected, washed and frozen with liquefied nitrogen. Five grams of the frozen cell bodies was ground with a mortar. The ground cell bodies was then mixed with 10 ml of a lysis buffer solution (100 mM Tris pH8, 100 mM EDTA, 100 mM NaCl, 100 g/mi of proteinase K) and incubated at 55° C for 3hrs. The resultant mixture was then extracted with phenol then with chloroform. To the aqueous layer was added ethanol gradually to precipitate pure genomic DNA. The DNA was collected and dissolved in a TE solution.

A hundred milligrams of the purified genomic DNA was partially digested with a restriction endonuclease Sau 3 AI. The resultant fragments were subjected to a 5 to 25% sucrose density gradient centrifugal separation (30,000rpm, 18 hr.) to obtain a 10 to 25 kbp DNA fragment. The fragment was then ligated to a BamHI arm of phage λ EMBL 3 (produced by Toyobo Co., Ltd. Japan). The λ phage DNA was packaged in vitro using a Gigapack Gold kit (produced by Stratagene) and infected to *E. coli* P2392 to afford the genomic DNA library of *C. hirsutus*.

EXAMPLE 4

Cloning of OCTase gener from genomic DNA library

The cloning of the genomic OCTase gene from the aforementioned genomic DNA library was conducted according to the conventional plaque hybridization method (Sambrook, Molecular Cloning A Laboratory Manual 2nd Ed., 1989).

The CDNA fragment cloned in example 2 was used as the probes after labeling with a radioisotope (32p) to select a positive clone. The cloning method was essentially same as described in example 1. The positive plaque was selected from the library by autoradiography to give six positive clones from 40,000 plaques. The phage DNA's were prepared from the positive clones by the conventional method, followed by the digestion with various restriction endonucleases and the Southern hybridization using the aforementioned 1.3 kbp cDNA probe to indicate the 5.5 kbp fragment of the restriction endonuclease Sal I digests was the positive DNA fragment.

The aforementioned 5.5 kbp Sal I fragment was then subcloned into the Sal I site of a plasmid vector pUC18 and transferred to *E. coli* JM109 by the conventional method. The DNA sequence of the subcloned DNA was then determined using a sequenase kit produced by United States Biochemical Co., Ltd.

The DNA sequence was depicted in SEQ ID NO: 4 to demonstrate that 4 introns interrupted the genomic DNA. the upstream region of the translation initiation site (653bp) several TATA-box like sequences, CAAT-box like sequences and cis-acting sequence related to the amino acid biosynthesis can be identified. The comparison of the open reading frame the genomic DNA with the OCTase cDNA sequence (consisting of 1125 bp of open reading frame) indicated 21 base changes between two OCTase genes. Only one amino acid substitution (Arg to Lys) was identified between the two OCTase genes since 20 of 21 base changes occur at the third position of the triplet codon, not affecting the deduced amino acids. However, the amino acid substitution could not affect the property of the enzyme since both amino acids are a basic amino acid. Therefore, these genes appear to be aileiic genes each other.

The aforementioned *E. coli* JM109/pUCR1 transformed with the aforementioned OCTase cDNA gene was deposited with National Institute of Bioscience and Human-Technology, Agency of Industrial Science and Technology as FERM P-12679 on Dec. 25, 1991, and transferred to an international deposition under the Budapest Treaty as FERM BP-4201 on Feb. 22, 1993.

EXAMPLE 5

Preparation of auxotrophic mutants

To induce fruit body formation, *C. hirsutus* (IFO 4917) was grown for eight weeks in a solid medium containing 20g of thermomechanical pulp of radiata pine supplemented with 130 ml of PD medium per 1 liter Erlenmeyer flask. The cultures were incubated at 28° C. and continuously illuminated using a 40w fluorescent lamp at a distance of 1m. *C. hirsutus* formed a typical fruit body under the culture condition described above.

Basidiospores were washed from gills with distilled water, filtered through 60 μm pore nylon cloth, diluted appropriately and plated onto PD agar medium. Monokaryons were screened under the microscope for mononucleate and clamp-lacking mycelia. The mating-type of each monokaryon was Getermined by means of confronting cultures between combinations of two monokaryons on SMY plate.

For oidia formation, a monokaryon was incubated on agar (1.3%) plates of MM supplemented with 1% casamino acid(Difco Laboratories, USA), pH 5.6, for 7-10 days at 28° C. Oidia were collected by rinsing the mycelial turf with distilled water, filtered through 60 μm pore nylon cloth and pelleted by centrifugation at 1,500×g for 10 min at room temperature.

The oidia ($2 \times 10^6$/ml) in 2 ml of phosphate buffer (10 mM, pH 7) were subjected with 50 μg/ml of N-methyl-N'-nitro-N-nitrosoguanidine (NTG) at 28° C. for 60 min with gentle stirring. This dose of NTG gave 3–5% survival of oidia in a series of mutagenesis treatment. The mutagenized oidia were washed three times with 10 ml of phosphate buffer by centrifugation (1,500×g, 10 min) and plated onto the agar and incubated at 28° C. After 2 days incubation, macroscopically visible colonies which grew on the MM agar plate were marked as prototrophs. Then 5ml of molten sort agar(1%, kept at 45°–48° C.) of MM supplemented with 1% casamino acid was overlaid onto the MM agar plate and further incubated. Colonies which grew on the overlay of complete medium, but not on the MM were screened as auxotrophic mutants.

To select amino acid requiring mutants, the auxotrophic mutants obtained were tested for growth on MM supplemented with one of five groups of L-amino acids, each at 150 μgh/mi. Colonies formed on these media were then transferred onto plates of MM containing individual amino acids or amino acid precursors (150 μg/ml) to identify specific supplement required. Thus, Arg⁻auxotrophic mutant was screened. Furthermore, a double-auxotrophic mutant (Arg⁻, Leu⁻) was prepared by NTG treatment of the Arg⁻auxotrophic mutant. These auxotrophic mutants were used as the recipient strain in the following transformation experiment.

EXAMPLE 6

Characterization of the double-auxotrophic mutant

The aforementioned mutant was studied to characterize the deficient gene in the arginine biosynthesis by the following method.

The mutant was cultured in the following five different media.

(1) MM+150 μg/ml leucine +200 μg/ml citrulline
(2) MM+150 μg/ml leucine +200 μg/ml ornithine
(3) MM+150 μg/ml leucine +200 μg/ml arginine
(4) MM+150 μg/ml leucine After 48 hr incubation at 28° C., the mutant in the media (1), (3) and (5) appeared to grow, whereas the mutant in the media (2) and (4) did not. Therefore, it was identified that the mutant was deficient in the ornithine carbamoyl transferase (OCTase) gene.

The aforementioned mutant (0JI-1078) is deposited with National Institute of Bioscience and Human-Technology, Agency of Industrial Science and Technology as FERM P-12677 on Dec. 25, 1991, and transferred to an international deposition under the Budapest Treaty as EERM BP-4210, on Mar. 1, 1993.

EXAMPLE 7

Transformation of Coriolus hirsutus 7-a

For mycelial protoplast preparation, mycelia (*C. hirsurtus* OJI-1078) were grown in 500 ml Erlenmeyer flasks containing 100ml of SMY medium equipped with thirty glass-beads (6mm in diameter) in a flask. The flasks were incubated statically for 7 days, while the flasks were stirred with gentle hand-shaking once or twice a day to prevent roycelia from forming pellets and aerial growth. Then the mycelia were transferred to 1 L Erlenmeyer flasks equipped with magnetic stir-bar, and cultured in 200m! of SMY medium.

7-b

Mycelia were harvested by suction filtration on 30 μm pore nylon cloth, and washed with osmotic medium (OM:0.5M MgSO₄/50mMmaleate buffer, pH 5.6). Mycelia(100 mg wet weight) suspended in lml of OM were treated with 10 mg/ml Novozyme 234 (Novo Nordisk Bioindustry Ltd., Japan) and 5 mg/ml Cellulase Onozuka R10 (Yakult Honsha, Japan) at 28° C. with gentle shaking for 4hrs.

7-c

Protoplasts were separated from mycelial debris by filtering through 30 μm pore nylon cloth. Mycelial debris and remaining protoplasts on nylon cloth were washed once by pouring OM to release protoplasts. Protoplasts were pelleted by centrifugation and suspended in 4 ml of 1M sucrose/20 mM MOPS buffer, pH 6.3(SM), washed twice with SM. The protoplasts were then resuspended in SM supplemented with 40 mM $CaCl_2$ (SMC) to give $10^7-10^8$ cells/ml and reserved at 4° C.

The number of protoplasts in suspension was determined by direct count in a hemacytometer. All centrifugations were at 1,000×g for 5 min with swinging buckets at room temperature.

For oidial protoplast preparation, $10^8$ cells of ungerminated oidia in 1ml of OM were treated as the same procedure for mycelial protoplast preparation as described above except that the nylon cloth filtration step was omitted. Protoplast viability ranged of 5–15%.

7-d

The aforementioned plasmid pUCR1 was digested with restriction enzyme Sal I. Then the DNA fragments (2 μg in 20 μl of 10 mM Tris/lmM EDTA[TE], pH 8.0) were added to the protoplast suspension($10^6$ cells/100 μl of SMC), mixed gently, and incubated on ice for 30 min.

The protoplasts suspension were gently mixed with ⅔ volume Of PEG solution (25% PEG ($M_r$=3,400 Aldrich Chemical Co., USA) buffered with 20mM MOPS (pH6.4)) and incubated for 30 min on ice.

The resultant protoplast solution was filled to 10 ml with MM containing 0.5M sucrose, 150 μg/ml leucine and 1% agar, poured over plates, and incubated at 28° C. for several days.

The transformants were obtained at a frequency of 300 colonies/μg DNA.

Similarly, using the circular plasmid pUCR1, the transformants were obtained at the same frequency. On the contrary, in the control experiment using pUCtl8 plasmid vector, no transformant was obtained.

EXAMPLE 8

Construction expression vector of lignin peroxidase (1)

The expression vector of lignin peroxidase of *C. hirsutus* was constructed by the ligation of the protein-coding sequence of the genomic lignin peroxidase (Japanese Patent Application 92-60503, pBSLPOG7, National Institute of Bioscience and Human-Technology, Agency of Industrial Science and Technology under FERM P-12683) to the downstream of the promoter region of the genomic phenoloxidase (Japanese Patent Application 91-15392, FERM BP-2793) as well as the upstream of the terminator region of the genomic phenoloxidase.

Figure 2:
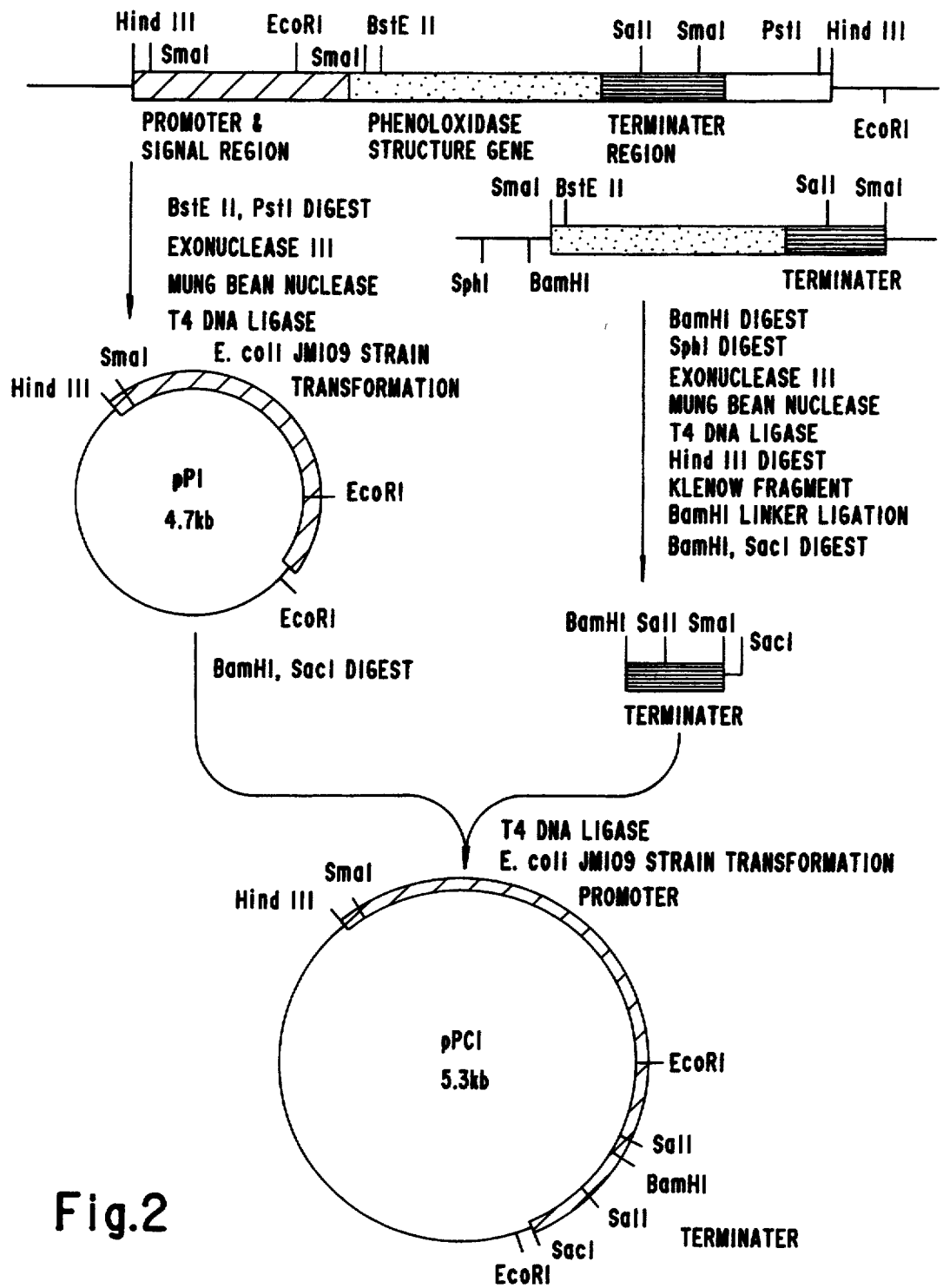
FIG. 2 is the construction of a expression vector, pPCl described in example 8.

Precisely speaking, 5.5 kbp DNA fragment of Hin dIII digests of the phenoloxidase genomic DNA was treated with exonuclease III and mung bean nuclease to remove the protein-coding region of the phenoloxidase followed by the ligation with T4DNA ligase to obtain a 2.0 kbp size plasmid pP1 containing the promoter region of the phenoloxidase (FIG. 2).

On the other hand, the aforementioned plasmid containing the genomic phenoloxidase gene was doubly digested with BamHI and Sph I, followed by the treatment with exonuclease III and mung bean nuclease, then the ligation with T4DNA ligase, and further digestion with Hin dIII to obtain a 600 bp size fragment containing the size terminator region of the phenoloxidase. This fragment was then inserted into the BamHI-Sac I site of the aforementioned plasmid pP1 to obtain the plasmid pPC1 (FIG. 2).

Furthermore, the reconbinant DNA pBSLPOG7 containing the genomic lignin peroxidase gene (Japanese Patent Application 92-60503) of *C. hirsutus* at the HI - Eco RI site of a E. Coli vector pBluescript SK+was treated with exonuclease III and mung bean nuclease to remove the promoter region of the lignin peroxidase followed by the ligation with Sal I linker and digestion with Sal I to obtain the protein-coding region of the lignin peroxidase.

Figure 3:
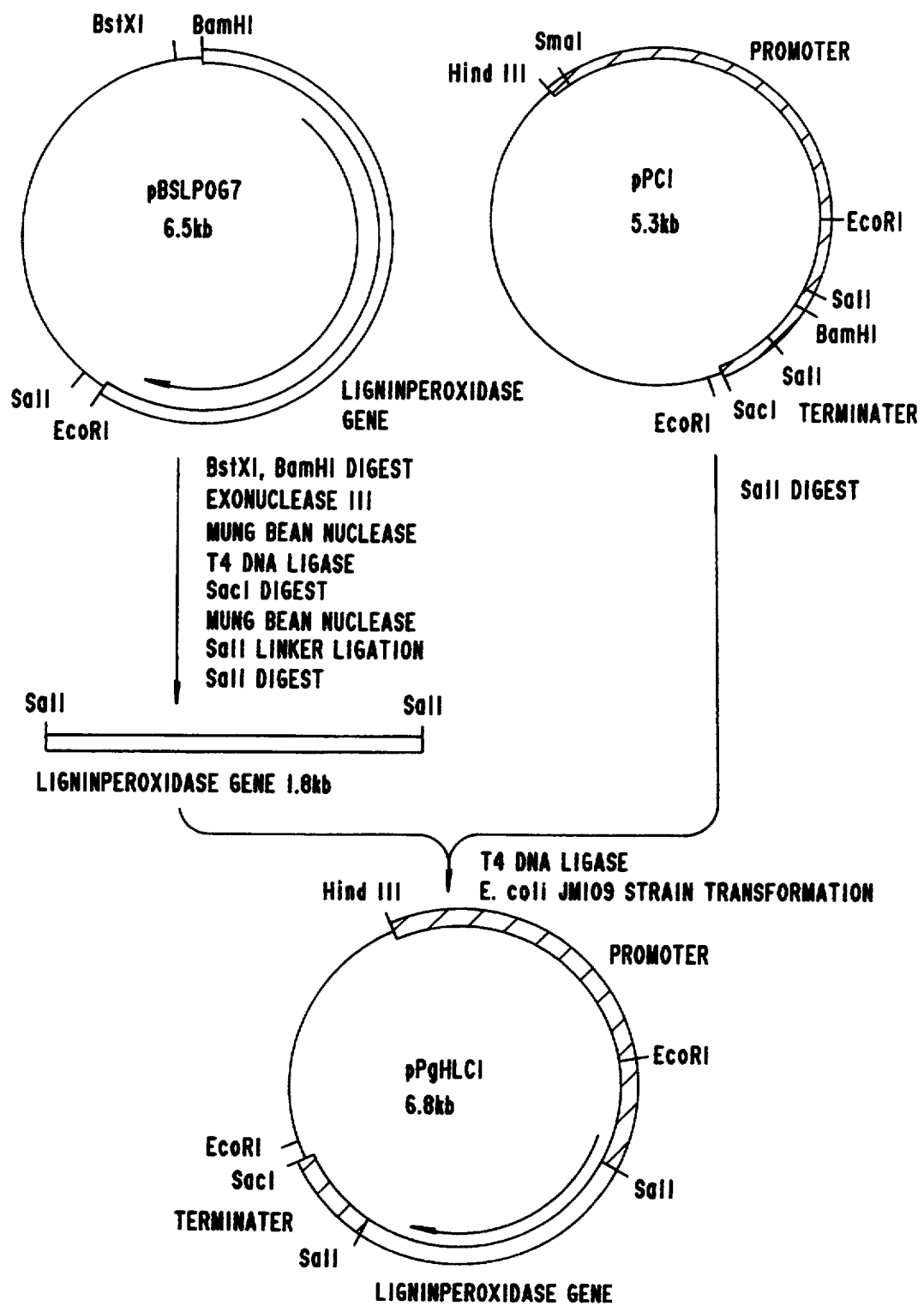
FIG. 3 is the construction of a lignin peroxidase expression vector, pPgHLCl described in example 8.
Figure 4:
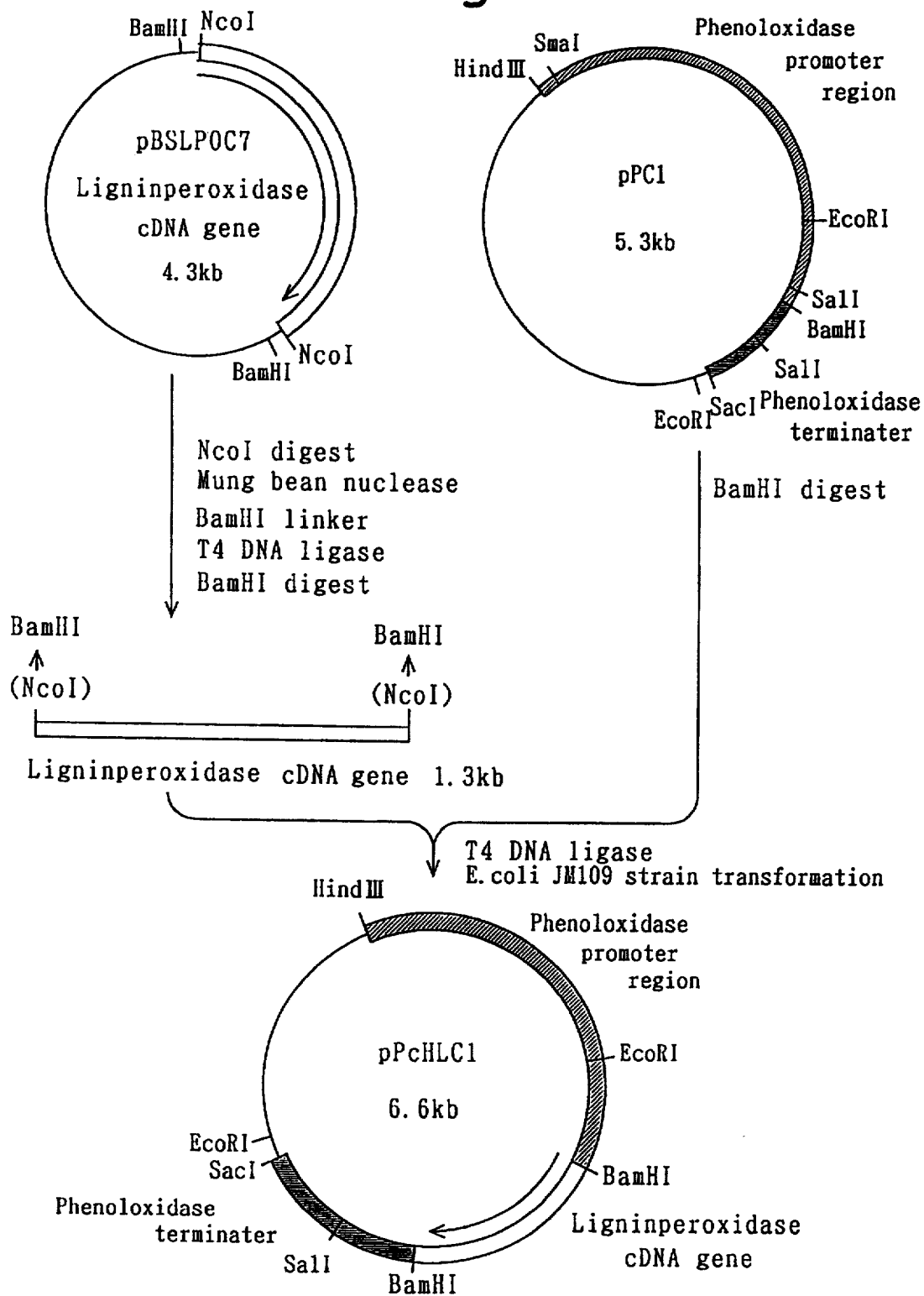
FIG. 4 is the construction of a lignin peroxidase expression vector, pPcHLCl described in example 9.

Finally, the plasmid pPC1 containing the promoter region and the terminator region of the phenoloxidase was digested with Sal I followed by the insertion of the aforementioned 1.8kbp lignin peroxidase- coding fragment to obtain the plasmid pPgHLC1 (FIG. 3)

EXAMPLE 9

Construction expression vector of lignin peroxidase (2)

The reconbinant DNA pBSLPOC7 (FERM P-12680) constructed by the subcloning of the cDNA gene (Japanese Patent Application 92-60503) of lignin peroxidase of *C. hirsutus* into the Bam HI site of a E. coli vector pBluescript SK+was digested with Nco I and treated with mung bean nuclease, followed by ligation to Bam HI linker with T4DNA ligase. The resultant DNA was digested with Barn HI to obtain 1.3 kbp fragment of the cDNA of the lignin peroxidase.

On the other hand, the plasmid pPC1 prepared in example 8 was digested with Bam HI and thereafter ligated with the aforementioned 1.3 kbp fragment of the cDNA of the lignin peroxidase to obtain the plasmid pPcHLC1.

EXAMPLE 10

Construction expression vector of ligning peroxidase (3)

The 5 5 kbp Hin dIII fragment of the phenoloxidase gene (Japanese Patent Application 3 - 15392, FERM P-12683 ) was ligated with T4DNA ligase to the Hin dIII site of phage vector M13mp19 to prepare a single-stranded phage DNA. The complement DNA of the signal-peptide-coding sequence o[the phenoloxidase (depicted in FIG. 5), consisting of 21 amino acids, was chemically synthesized using a DNA synthesizer. This DNA primer was annealed to the aforementioned single-strand phage DNA to obtain the DNA fragment of the promoter sequence and the signal-coding sequence using the primer extension method. The resultant DNA was digested with Hin dIII to obtain 2.1 kbp DNA fragment (Fragment 1).

On the other hand, to obtain the protein-coding DNA sequence of the lignin peroxidase, the plasmid pBSLPOG7 (Japanese Patent Application 92-60503, FERM P-12683) was treated by the essentially same method as described above (depicted in FIG. 5). Thus, the primer extension method and digestion with Sal I to obtain 1.7 kbp DNA fragment (Fragment 2).

The aforementioned two fragments 1 and 2 were then ligated with T4DNA ligase to the E. coli vector pUC18 doubly digested with Hin dIII and Sal I to obtain the plasmid pPSgHL1 containing both fragments (depicted in FIG. 5).

EXAMPLE 11

Construction expression vector of lignin peroxidase (4)

To obtain the propeptide-containing DNA sequence of the lignin peroxidase the plasmid pBSLPOG7 (Japanese Patent Application 92-60503, FERM P-12683) was treated by the essentially same method as described above (depicted in FIG. 6). Thus, the primer extension method and digestion with Sal I to obtain 1.7 kbp DNA fragment (Fragment 3).

The aforementioned two fragments 1 and 3 were then ligated with T4DNA ligase to the E. coli vector pUC18 doubly digested with Hin dIII and Sal I to obtain the plasmid pBSproHL1 containing both fragments (depicted in FIG. 6).

EXAMPLE 12

Construction expression vector of lignin peroxidase (5)

The expression vector pRPgHL1 of lignin peroxidase of C. hirsutus was constructed by the ligation of the protein-coding sequence of the lignin peroxidase to the downstream to the promote sequence of the OCTase gene of C. hirsutus.

In detail, the promoter fragment was prepared by the essentially same method as described in example 10. Thus, the primer extension method and digestion with Eco RI to obtain 0.6 kbp DNA fragment (Fragment 4, depicted in FIG. 7).

The protein-coding sequence of lignin peroxidase was prepared by the primer extension method and digestion with Hin dIII to obtain 1.7 kbp DNA fragment (Fragment 5, depicted in FIG. 6 ).

The aforementioned two fragments 4 and 5 were then ligated with T4DNA ligase to the E. coli vector pUC1.9 doubly digested with Eco RI and Hin dIII to obtain the plasmid pRPgHL1 containing both fragments (depicted in FIG. 7).

EXAMPLE 13

Construction expression vector of lignin peroxidase (6)

The plasmid pUCR1 containing the OCTase gene was digested with Eco RI and the cohesive site was treated with Klenow Fragment to give blunt ends. Then Hin dIII linker (8 mer) was ligated to the plasmid to make a Hin dIII site. In addition, this plasmid was digested with Sal I and the cohesive site was treated with Klenow Fragment to give blunt ends followed by the self-ligation to remove Sal I site.

Figure 8:
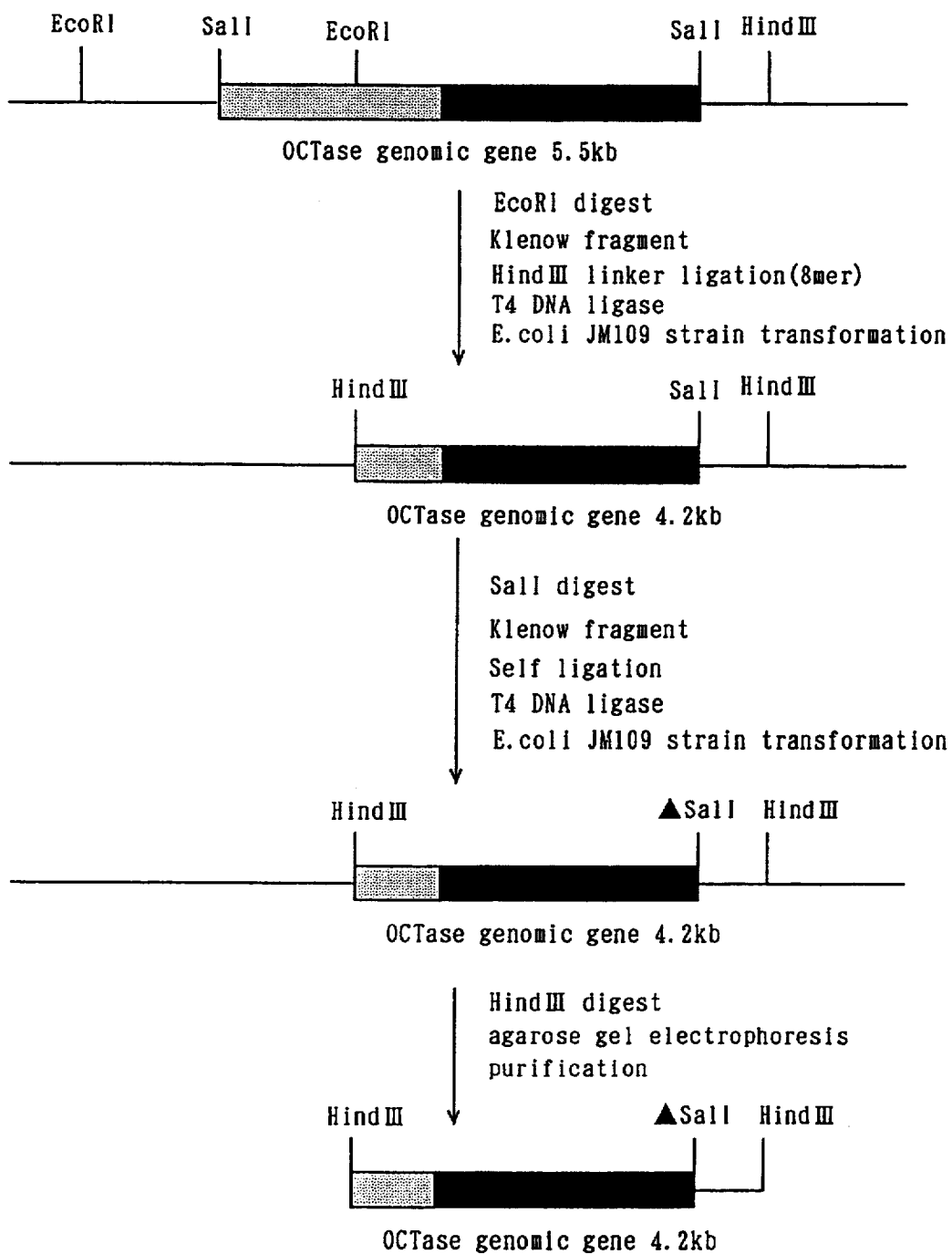
FIG. 8 is the construction of a fragment of OCTase gene described in example 13.
Figure 9:
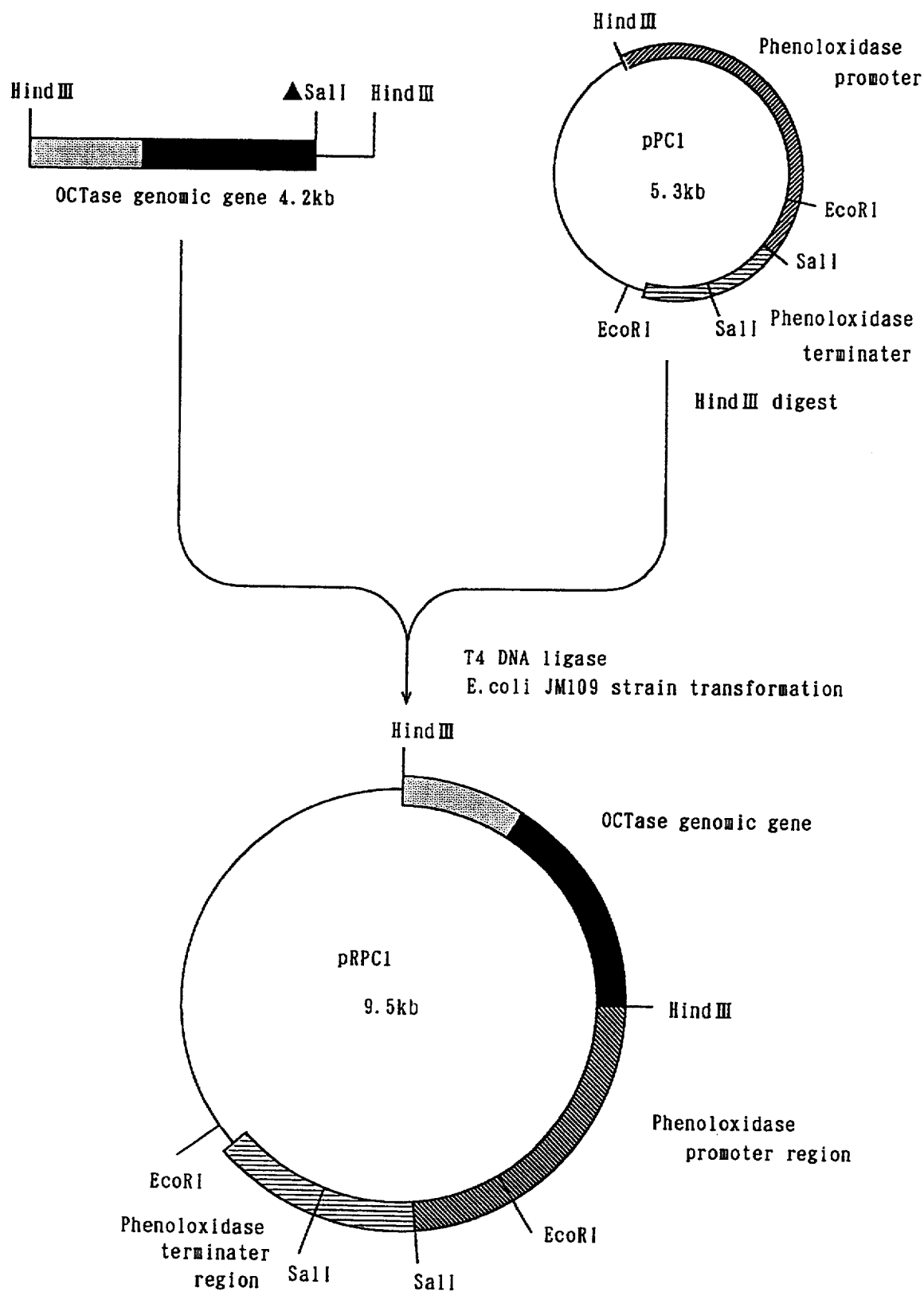
FIG. 9 is the recombinant DNA pRPCl described in example 13.
Figure 10:
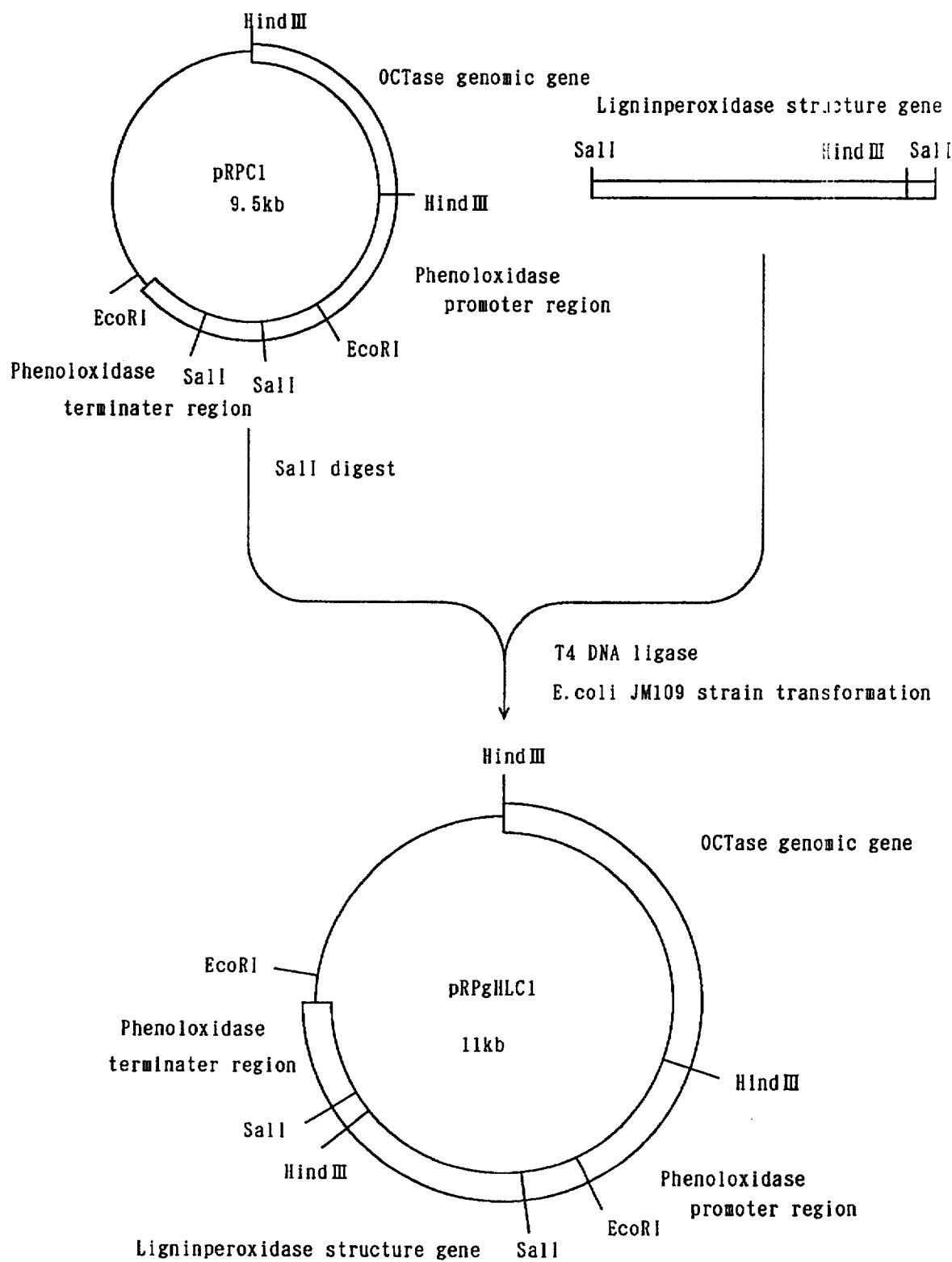
FIG. 10 is the construction of a lignin peroxidase expression vector pRPgHLCl described in example 13.

The aforementioned recombinant DNA was then digested with Hin dIII to obtain the 4.2 kbp DNA fragment containing the OCTase gene (depicted in FIG. 8). This fragment was inserted into the Hin dIII site of the plasmid prepared in example 8 to obtain the recombinant DNA pRPC1 (depicted in FIG. 9). The 1.8 kbp DNA fragment containing the protein-coding regmon of lignin peroxidase ( prepared in example 8) was inserted into the Sal I site of the plasmid pRPC1 to obtain the lignin peroxidase expression vector pRPgHLC1 (depicted in FIG. 10).

EXAMPLE 14

Preparation of C. hirsutus transformed with the lignin peroxidase expression vector The plasmids, pPgHLC1, pPcHLC1, pPSgHL1, pPSproHL1, and pRPgHL1 (prepared in examples 8, 9, 10, 11, and 12, respectively) were co-transformed with the plasmid pUCR1 containing the OCTase gene of C. hirsutus as the marker to the Arg⁻auxotrophic mutant OJI-1078 of C. hirsutus, using the PEG method or the electroporation method, to give the transformants pPgHLCl/OJI - 107 8, pPcHLCl/OJI - 107 8, pPSgHL1/OJI 107 8, pPSproHL1/OJI - 107 8, and DRPgHL1/OJI - 107 8, respectively. The plasmid pRPgHLC1 ( prepared in Example 13) was transformed to the aforementioned OJI-1078, using the PEG method or the electroporation method, to give the transformants pRPgHLC1/OJI-1078. The aforementioned transformations were successful in spite of the form of the plasmids, such as the circular or the linear. The transformation condition was as described below.

To 100 μl of protoplast suspension (about $10^7$ plotoplasts/100 μl was added 2 μg of plasmid (circular or linear form) as well as 0.2 μg of plasmid pUCR1 as the selection marker. The mixture was kept on ice for 30 min. In the case of plasmid pRPgHLC1 ( prepared in Example 13 ), only 2 μg of plasmid pRPgHLC1 was added to the protoplasts and kept on ice for 30 min. To the resultant mixture was added the same volume of PEG solution (50% PEG3400, 20 mM pH 6.4 MOPS) and kept on ice for 30 min. The resultant protoplast solution was filled to 10 ml with MM containing 0.5M sucrose, 150 μg/m leucine and 1% agar, poured over plates, and incubated at 28° C. for four days to obtain the transformants.

The transformation of the plasmid containing lignin peroxidase was confirmed by the Southern hybridization of the genomic DNA of the transformant.

EXAMPLE 15

Culture of the transformant and activity of the lignin peroxidase

The five transformants, pPgHLCl/OJI- 1078, pPcHLCl/OJi 107 8, pPSgHL1/OJI - 107 8, pPSproHL1/OJI - 107 8, and pRPgHL1/OJI1078, prepared in example 14, were shaken-cultured in 100 ml of a GP medium (described in example 1) at 28° C. for 7 days. The resultant culture broth was centrifuged to give the supernatant.

On the other hand, the transformants pRPgHLC1/OJI-1078 was cultured in 100ml of the synthetic medium described in Example 1 at 28° C. for 10 days. The resultant culture broth was centrifuged to give the culture supernatant.

The activity of lignin peroxidase was measured as described below. To a solution consisting of 50 μl of 8 mM veratryl alcohol and 200 μl of 0.5M, pH3, sodium tartrate buffer, was added 700 μl of the culture supernatant and 50 μl of 5.4 mM hydrogenperoxide, successively. The activity ( 1 unit: production of 1 μmol/L.-min ) of lignin peroxidase was measured for the increase of the absorption at 310 nm resulting from the oxidation of veratryl alcohol to veratraldehyde. The activities of the lignin peroxidase of the aforementioned culture supernatant of the transformants were in a range of 20–100 units/mi. Whereas, in the case of the control experiment culturing C. hirsutus OJI-1078 without the transformation of the plasmid, no lignin peroxidase activity was observed.

EXAMPLE 16

Construction of phenoloxidase expression vector

The genomic OCTase gene of C. hirsutus contains a promoter region at the 2 kbp upstream of the initiation codon ATG. Therefore, this promoter can be connected to the phenoloxidase gene consisting of the signal-peptide-coding sequence and the protein-coding sequence for the secretionai production of phenoloxidase of C. hirsutus OJI-1078.

In detail, the 5.5 kbp Sal I fragment of the OCTase gene was ligated with T4DNA ligase to the Sal I site of phage vector M13mp19, then the complementary DNA was synthesized using the primer extension method and the resultant DNA was digested with Eco RI to obtain 0.6 kbp DNA fragment (Fragmen5 4, depicted in Example 10).

On the other hand, a plasmid containing the genomic phenoloxidase was digested with Eco RI to obtain the 4.2 kbp DNA fragment of the protein-coding region of the phenoloxldase (fragment 6).

Figure 11:
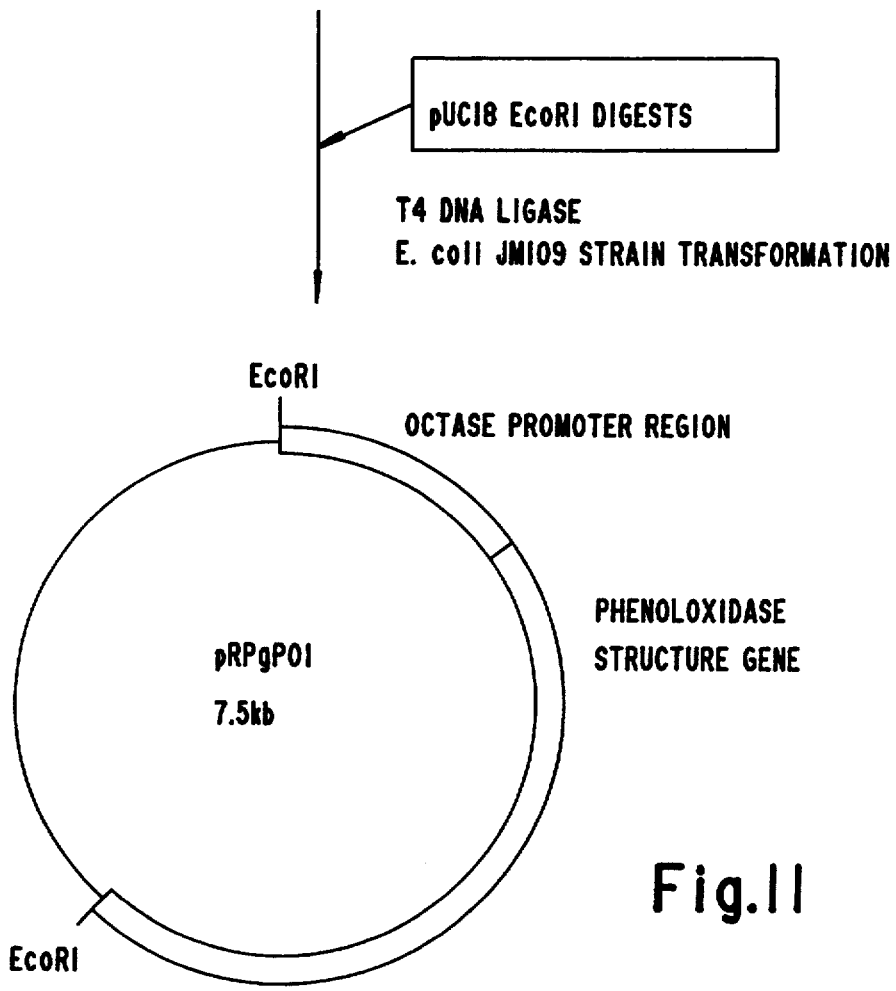
FIG. 11 is the construction of a phenoloxidase expression vector pRPgPO1 described in example 16.

The aforementioned two fragments 4 and 6 were then ligated with T4DNA ligase to the E. coli vector pUCI8 digested with Eco RI to obtain the plasmid pRPgPOl containing both fragments (depicted in FIG. 11 ).

EXAMPLE 17

Preparation of the transformed C. hirsutus using the phenoloxidase expression vector The aforementioned plasmid pRPPOMl was transformed to C. hirsutus OJI-1078 by the method as described in example 14 to obtain the transformant pRcPO1/OJI-1078.

In addition, the genomic phenoloxidase gene pPOl(-Japanese Patent Application, FERM BP-2793) was also transformed to C. hirsutus OJI-1078 to obtain the transformant pPO1/OJI-1078 for the purpose of the gene dosage effect.

EXAMPLE 18

Secretional production of phenoloxidase and activity of phenoloxidase

The transformants pRcPOl/OJI-1078 prepared in Example 17 was shaken-cultured at 28° C. for 20 days in 100 ml of the synthetic medium described in Example 1. The resultant culture broth was centrifuged to give the culture supernatant.

Similarly, the transformants pPOl/OJI-1078 was cultured in the aforementioned GP medium to the culture supernatant.

The phenoloxidase activities of the both culture supernatants were 20-50% higher than those of the control experiments using C. hirsutus OJI-1078 without the transformation of the plasmids.

EXAMPLE 19

Construction of expression plasmid of luciferase

Figure 12:
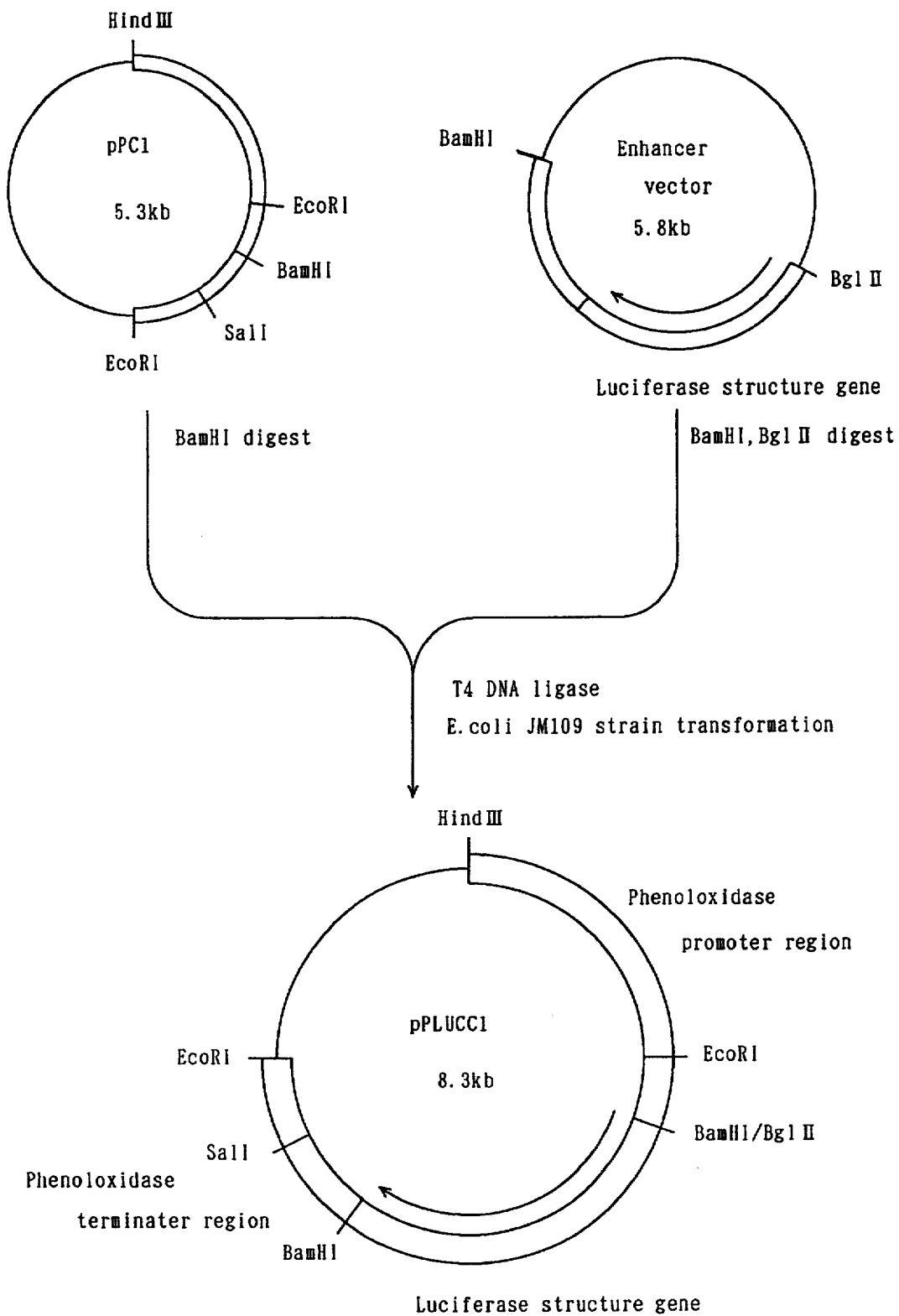
FIG. 12 is the construction of a luciferase expression vector pPLUCCl described in example 19.

A commercially available enhancer vector (Pica Gene produced by Toyo Ink Co. Ltd., Japan), containing luciferase gene was digested with restriction endonucleases BamHI and Bg1lII to obtain the 3 kbp DNA fragment of the luciferase structural gene. The fragment was then subcloned at the BamHi site of plasmid ppC1 prepared in Example 8, to obtain the luciferase expression plasmid designated as DPLUCC1 ( depicted in FIG. 12).

EXAMPLE 20

Preparation of transformed C. hirsutus OJI-1078 with pPLUCC1 and luciferase activity C. hirsutus OJI - 1078 was co-transformed with the plasmids pPLUCC1 and pUCR1. The transformant was cultured in 100 ml of GP medium described in the experiment 1, and was shaken-cultured at 28° C. for 7 days.

The cells were harvested by centrifugation, washed with sterilized water, and frozen with liquefied nitrogen. The cell bodies were ground with a mortar. The ground cell was transferred to 30 ml centrifugation tube, suspended in a cell extraction buffer (25ram Tris-phosphate, pH 7.8, 2mM DTT, 2ram 2-diaminocyclohexane-N, N,N', N'-tetraacetic acids 10% glycerol, 1% Triton X-100), and then left at roon: temperature for 10 to 15 min. The resultant mixture was centrifuged to remove mycelial debris. Finally, to 20 μl of the supernatant was added the 100 μl of a luciferin solution (attached in the kit) to give luminescence in a darkroom indicating the expression of the luciferase.

---

We claim:

1. An isolated DNA sequence coding for ornithine carbamoyl transferase (OCTase) of *Coriolus hirsutus*, wherein the DNA sequence encodes an amino acid sequence having the amino acid sequence shown in SEQ ID no: 1 or SEQ ID No: 2.

2. An isolated DNA sequence comprising the following, operably linked in the 5' to 3' direction: a promoter, an OCTase coding region of *C. hirsutus* and a transcription termination region, wherein the OCTase coding region encodes an amino acid sequence having the amino acid sequence shown in SEQ ID No: 1 or SEQ ID No: 2.

3. An isolated recombinant linear or circular DNA comprising:
   (1) an OCTase coding region of *C. hirsutus*; or
   (2) a DNA sequence comprising he following, operably linked in the 5' to 3' direction: a promoter, an OCTase coding region of *C. hirsutus* and a transcription termination region,
wherein the OCTase coding region encodes an amino acid sequence having the amino acid sequence shown in SEQ ID No: 1 or SEQ ID No: 2.

4. An isolated recombinant circular DNA according to claim 3, wherein the DNA is a plasmid.

5. An isolated recombinant linear or circular DNA comprising:
   (1) an OCTase coding region of *C. hirsutus*; or a DNA sequence comprising the following, operably linked in the 5' to 3' direction: a first promoter, an OCTase coding region of *C. hirsutus* and a transcription termination region;
   (2) a second promoter operable in a basidiomycete of the genus Coriolus; and
   (3) a coding region coding for a desired protein under control by the second promoter, wherein the OCTase coding region encodes an amino acid sequence having the amino acid sequence shown in SEQ ID No: 1 or SEQ ID No: 2; wherein the first promoter may be the same or different from the second promoter.

6. An isolated recombinant linear or circular DNA according to claim 5, wherein the second promoter is a promoter selected from the group consisting of a promoter of phenoloxidase gene, a promoter of lignin peroxidase gene an a promoter of OCTase gene.

7. A recombinant linear or circular DNA according to claim 5, wherein the recombinant linear or circular DNA further comprises a DNA sequence coding for a signal peptide present upstream of the coding region for the desired protein and linked in frame with the coding region for the desired protein.

8. A recombinant linear or circular DNA according to claim 7 wherein the signal peptide is selected from the group consisting of a signal peptide of phenoloxidase and a signal peptide of lignin peroxidase.

9. An auxotrophic mutant, OJI-1078 (FERM BP-4210), of a basidiomycete of the genus Coriolus deficient in an ability to express OCTase.

10. A host-vector system comprising:
   (1) a DNA sequence comprising the following, operably linked in the 5' to 3' direction: a promoter, an OCTase coding region of *C. hirsutus* and a transcription termination region, wherein the OCTase coding region encodes an amino acid sequence having the amino acid sequence shown in SEQ ID No: 1 or SEQ ID No: 2; and
   (2) an auxotrophic mutant, OJI-1078 (FERM BP-4210), of the genus Coriolus deficient in an ability to express OCTase.

11. A host-vector system for expression of a desired protein according to claim 10, further comprising the following, operably linked in the 5' to 3' direction; a promoter, a coding region coding for the desired protein and a transcription termination region.

12. A process for production of a transformant basidiomycete of the genus Coriolus capable of expressing a desired protein, comprising the steps of:
   (a) cotransforming an auxotrophic mutant, OJI-1078 (FERM BP-4210), of a basidiomycete of the genus Coriolus deficient in an abilityto express OCTase, with:
      (1) a linear or circular DNA sequence comprising the following, operably linked in the 5' to 3' direction: a promoter, an OCTase coding region of *C. hirsutus* and a transcription termination region, and
      (2) a linear or circular DNA comprising the following, operably linked in the 5' to 3' direction: a promoter, a coding region encoding the desired protein, and a transcription termination region; and
   (b) selecting a transformant capable of growing in a medium lacking arginine.

13. A process for production of a transformant basidiomycete of the genus Coriolus capable of expressing a desired protein, comprising the steps of:
   (a) transforming an auxotrophic mutant, OJI-1078 (FERM BP-4210), of a basidiomycete of the genus Coriolus deficient in an ability to express OCTase, with a linear or circular DNA comprising:
      (1) an OCTase coding region of *C. hirsutus*, or a DNA sequence comprising the following operably linked in the 5' to 3' direction: a first promoter, an OCTase coding region of *C. hirsutus* and a transcription termination region;
      (2) a second promoter operable in a basidiomycete of the genus Coriolus; and (3) a coding region for the desired protein under the control by the second promoter; and (b) selecting a transformant capable of growing a medium lacking arginine, wherein the first promoter may be the same as or different from the second promoter.

14. A transformant basidiomycete obtained by a process according to claim 12, which produces a desired protein.

15. A transformant basidiomycete obtained by a process according to claim 13, which produces a desired protein.

16. A process for production of a desired protein, comprising the steps of:
culturing a transformant basidiomycete according to claim 14 to produce the desired protein; and
recovering the desired protein from the culture.

17. A process for production of a desired protein, comprising the steps of:
culturing a transformant basidiomycete according to claim 15, to produce the desired protein; and
recovering the desired protein from the culture.

* * * * *